United States Patent
Meron et al.

(10) Patent No.: US 10,118,002 B2
(45) Date of Patent: *Nov. 6, 2018

(54) DEVICES FOR INJECTING A SUBSTANCE AND METHODS THEREFOR

(71) Applicant: Ethicon, Inc., Somerville, NJ (US)

(72) Inventors: Moti Meron, Herzliah (IL); Israel Nur, Moshav Timmorim (IL); Roee Atlas, Givatayim (IL)

(73) Assignees: Ethicon Inc., Somerville, NJ (US); Omrix Biopharmaceuticals Ltd., Rehovot (IL)

( * ) Notice: Subject to any disclaimer, the term of this patent is extended or adjusted under 35 U.S.C. 154(b) by 289 days.

This patent is subject to a terminal disclaimer.

(21) Appl. No.: 15/007,346

(22) Filed: Jan. 27, 2016

(65) Prior Publication Data
US 2016/0136360 A1    May 19, 2016

Related U.S. Application Data

(63) Continuation of application No. 13/053,448, filed on Mar. 22, 2011, now Pat. No. 9,278,181.
(Continued)

(30) Foreign Application Priority Data

May 26, 2010    (EP) .................................... 10250976

(51) Int. Cl.
*A61M 5/32*    (2006.01)
*A61M 5/24*    (2006.01)
(Continued)

(52) U.S. Cl.
CPC ..... *A61M 5/3294* (2013.01); *A61B 17/00491* (2013.01); *A61M 5/19* (2013.01);
(Continued)

(58) Field of Classification Search
CPC .... A61M 5/19; A61M 5/2448; A61M 5/3294; A61M 5/31596; A61M 5/322; A61M 5/31578
(Continued)

(56) References Cited

U.S. PATENT DOCUMENTS 3,572,336 A    3/1971    Hershberg
4,026,288 A    5/1977    Costa et al.
(Continued)

FOREIGN PATENT DOCUMENTS

EP    1845860    11/2009
JP    07-067961    3/1995
(Continued)

OTHER PUBLICATIONS

EP Search Report issued by the European Patent Office in corresponding EP 10250976.7, dated Mar. 15, 2011.
(Continued)

*Primary Examiner* — Nathan R Price
*Assistant Examiner* — Anh Bui
(74) *Attorney, Agent, or Firm* — Doherty IP Law Group LLC

(57) ABSTRACT

A device for administering injections includes a housing having an upper end, a lower end including a bottom surface with an injection needle opening, and an axis extending between the upper and lower ends. The device includes a needle housing with an injection needle. The needle housing is disposed within the housing for moving between a retracted position and an extended position. The device has an injection actuator for commencing an injection cycle including a first stage in which the needle housing and said plunger base are coupled together and move in a first direction along the axis and a second stage in which the needle housing and the plunger base are decoupled from one
(Continued)

another so that the plunger base is free to move away from the needle housing in a second direction that is opposite the first direction.

20 Claims, 21 Drawing Sheets

Related U.S. Application Data

(60) Provisional application No. 61/316,881, filed on Mar. 24, 2010.

(51) Int. Cl.
*A61B 17/00* (2006.01)
*A61M 5/19* (2006.01)
*A61M 5/315* (2006.01)
*A61M 5/31* (2006.01)
*A61M 5/20* (2006.01)
*A61M 5/46* (2006.01)

(52) U.S. Cl.
CPC ...... *A61M 5/2448* (2013.01); *A61M 5/31578* (2013.01); *A61M 5/31581* (2013.01); *A61M 5/31596* (2013.01); *A61M 5/322* (2013.01); *A61M 5/3257* (2013.01); *A61M 5/3287* (2013.01); *A61M 5/3293* (2013.01); *A61M 5/204* (2013.01); *A61M 5/326* (2013.01); *A61M 5/46* (2013.01); *A61M 2005/3128* (2013.01); *A61M 2005/3206* (2013.01)

(58) Field of Classification Search
USPC .................................................. 604/82, 191
See application file for complete search history.

(56) References Cited

U.S. PATENT DOCUMENTS

| | | | |
|---|---|---|---|
| 4,359,049 A | 11/1982 | Redl et al. | |
| 4,609,371 A | 9/1986 | Pizzino | |
| 4,738,660 A * | 4/1988 | Lucas ................ | A61M 5/2033 604/139 |
| 5,298,023 A | 3/1994 | Haber et al. | |
| 5,322,510 A | 6/1994 | Lindner et al. | |
| 5,749,968 A | 5/1998 | Melanson et al. | |
| 6,527,749 B1 | 3/2003 | Roby et al. | |
| 6,599,272 B1 * | 7/2003 | Hjertman ............... | A61M 5/315 604/197 |
| 6,783,514 B2 | 8/2004 | Tovey et al. | |
| 9,278,181 B2 * | 3/2016 | Meron ............ | A61B 17/00491 |
| 2004/0064102 A1 | 4/2004 | Yamada | |
| 2004/0069044 A1 * | 4/2004 | Lavi ........................ | A61M 5/19 73/1.73 |
| 2006/0015067 A1 | 1/2006 | Bates | |
| 2006/0015085 A1 | 1/2006 | Bates | |
| 2008/0154201 A1 | 6/2008 | Bates | |
| 2008/0306436 A1 | 12/2008 | Edwards et al. | |
| 2009/0221914 A1 * | 9/2009 | Barrett .................. | A61M 5/007 600/431 |
| 2010/0137796 A1 | 6/2010 | Perry et al. | |
| 2010/0331773 A1 | 12/2010 | Frederiksen et al. | |
| 2011/0238009 A1 | 9/2011 | Meron et al. | |
| 2011/0282324 A1 | 11/2011 | Kurokawa et al. | |
| 2011/0282381 A1 | 11/2011 | Cronin et al. | |
| 2012/0215248 A1 | 8/2012 | Perry et al. | |
| 2012/0253182 A1 | 10/2012 | Patrick et al. | |

FOREIGN PATENT DOCUMENTS

| | | |
|---|---|---|
| JP | 10511014 | 10/1998 |
| JP | 2002543931 | 12/2002 |
| JP | 2004065737 | 3/2004 |
| JP | 2008528210 | 7/2008 |
| JP | 2008-540117 | 11/2008 |
| WO | WO 0069488 | 11/2000 |
| WO | WO 2006020256 | 2/2006 |
| WO | WO 2007059801 | 5/2007 |

OTHER PUBLICATIONS

English language translation of Office Action—Notification of Reasons for Refusal, issued by the Japanese Patent Office in corresponding Japanese Patent Application 2013-500655, dated Jan. 6, 2015, 4 pages.

International Search Report issued by the International Searching Authority in International Application No. PCT/IL2011/000268, dated Oct. 7, 2011, 8 pages.

Written Opinion issued by the International Searching Authority in International Application No. PCT/IL2011/000268, dated Sep. 25, 2012, 12 pages.

* cited by examiner

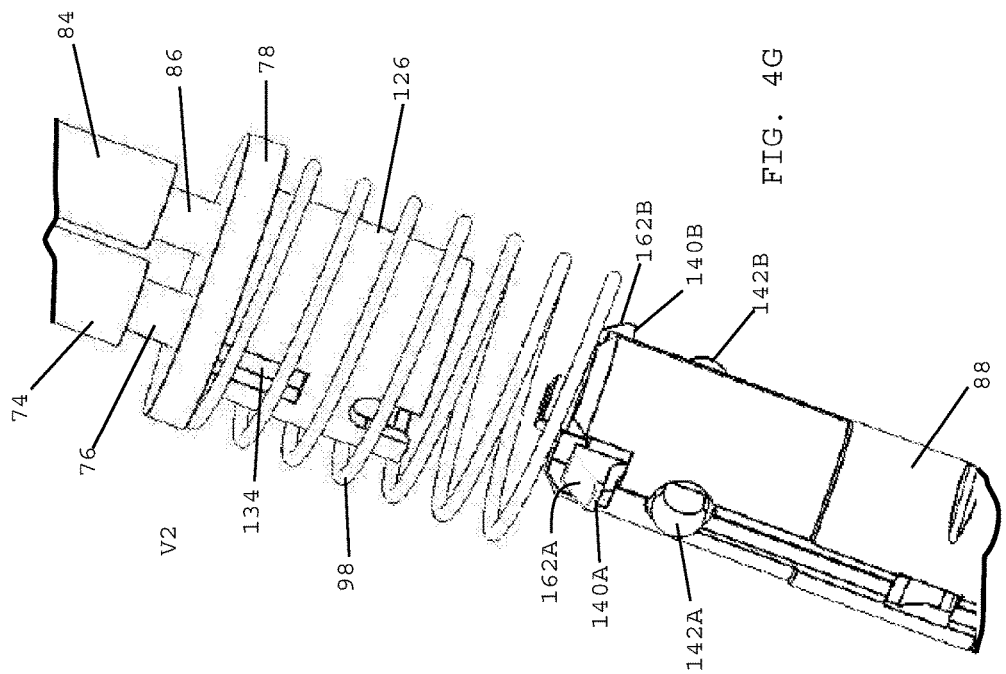
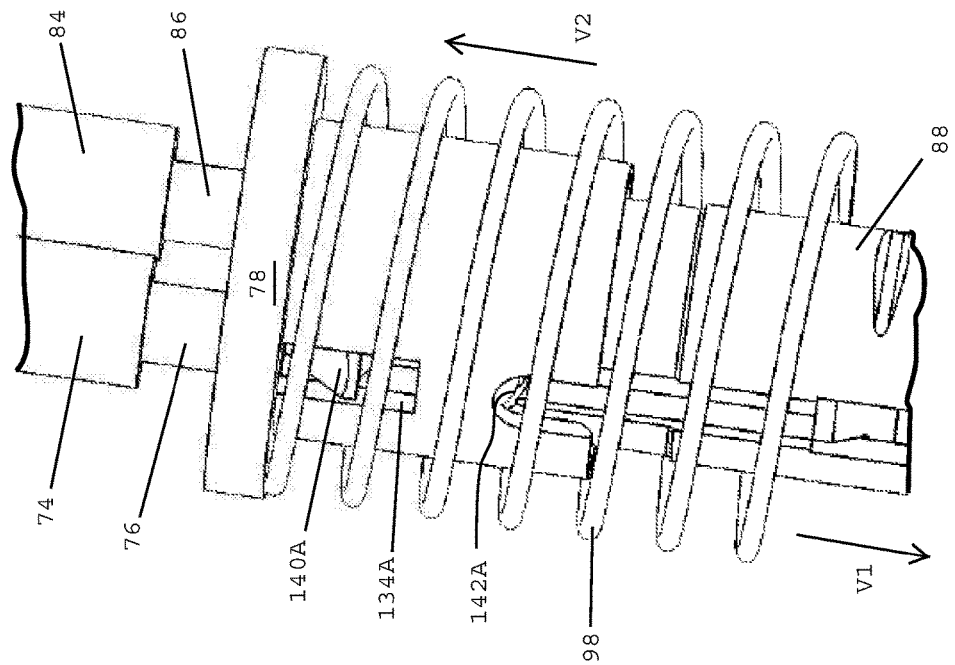

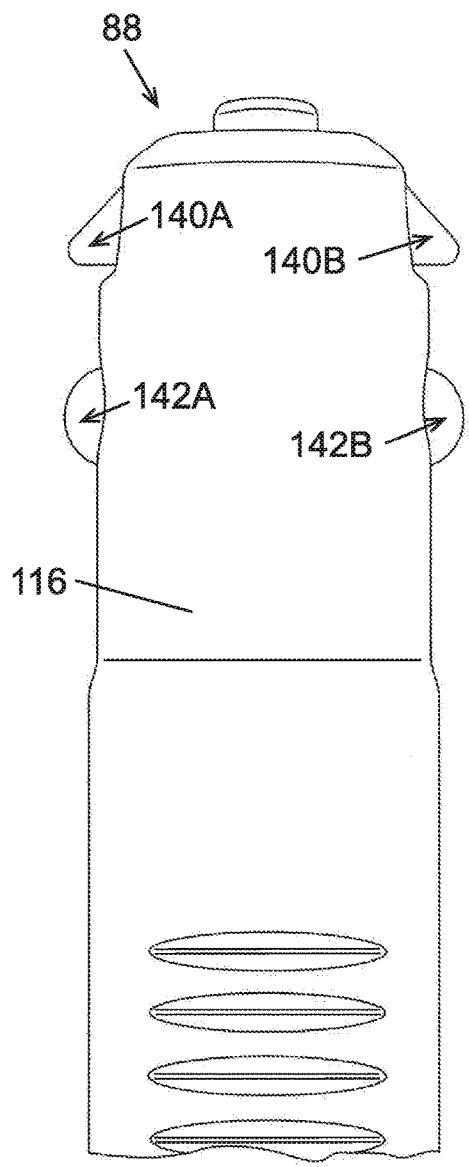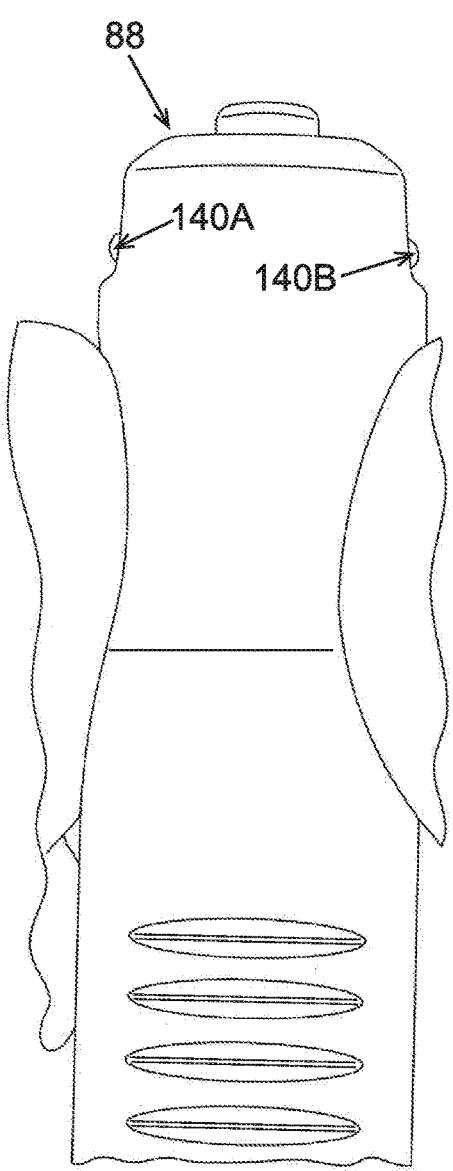

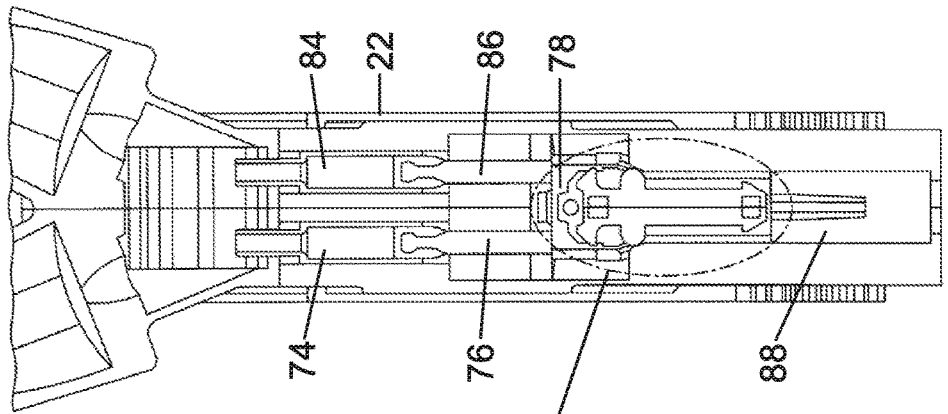
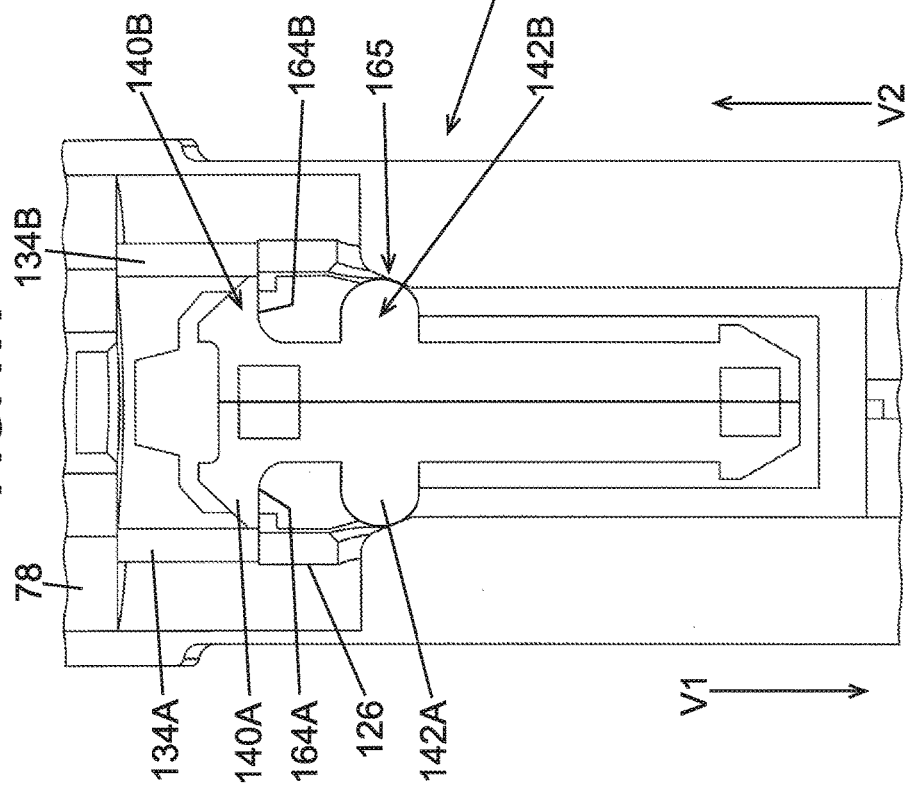

DEVICES FOR INJECTING A SUBSTANCE AND METHODS THEREFOR

CROSS REFERENCE TO RELATED APPLICATIONS

The present patent application is a continuation of U.S. patent application Ser. No. 13/053,448, filed Mar. 22, 2011, now allowed, which claims the benefit of U.S. Provisional Application Ser. No. 61/316,881, filed Mar. 24, 2010, the disclosures of which are hereby incorporated by reference herein. U.S. patent application Ser. No. 13/053,448 also claimed priority to European Application Number EP 10250976, filed May 26, 2010.

BACKGROUND OF THE INVENTION

Field of the Invention

The present application generally relates to injections, and more specifically relates to medical devices for administering multiple injections.

Description of the Related Art

Many patients are required to receive injections whereby the injected substance includes two or more components. In many instances, the two or more components must be stored separate from one another, but are mixed together immediately prior to injecting the combined components into a tissue. For example, diabetic patients often receive injections having two different components that must be separated prior to injection. More specifically, it is known that fibrinogen and thrombin may be injected to form a fibrin polymer in-situ so as to induce angiogenesis. Due to the fact that fibrinogen and thrombin will rapidly polymerize upon interaction, it is critical that the two components be maintained apart from one another until applied at the application site.

Providing injections having two or more components are further complicated by the fact that the dosage requirements vary from patient to patient, or even for the same patient. Attempts to combine the separate components into a final, injectable solution often result in contamination of one or more of the individual components. In addition, attempts to address the administration of two or more medications in liquid form may require administering multiple injections into a patient in order to reach the recommended dose, a first injection for the first component and simultaneously a second injection for the second component. Administering multiple injections every time an injection is required is time consuming, may result in improper mixing of components, and may cause tissue damage.

A number of devices have been developed for maintaining at least two substances apart from one another before being injected. For example, U.S. Pat. No. 4,359,049 to Redl et al. teaches a device that holds two syringes together in a support having a common actuator. The dispensing end of each of the syringes is inserted into a collection manifold where the two separate substances are mixed together. The mixed substances are then dispensed through a common needle inserted into an application site.

U.S. Pat. No. 4,609,371 to Pizzino discloses a device including a dual syringe that provides for the simultaneous or sequential injection of two different injectable liquids. The dual syringe includes two barrels, each having a plunger for the injection of a liquid, and a manually operable three-position rotary valve that controls the filling of the syringe and the outflow of the liquid from the syringe. The valve has three different positions for enabling the liquid to be dispensed either from the first barrel only, the second barrel only, or both barrels simultaneously.

Commonly assigned EP 1 845 860, the disclosure of which is hereby incorporated by reference herein, teaches an applicator device for applying a multi-component fluid, especially a multi-component tissue glue, including a plurality of substantially cylindrical supply containers for respectively one component of the fluid to be applied. Each supply container has a front end with an out-let opening, a rear end opposite to the front end, and a slidably displaceable piston arranged within the supply container and having a piston rod extending out of the rear end for operating the piston. The applicator device includes a manifold having terminal ends with a first port for fluid connection with the front ends of the supply containers. The manifold also has internal channels extending from the first ports of the terminal ends to an outlet site. The applicator device includes a holding element for holding the supply containers, and a coupling element extending from the holding element and having a connection end connected to the manifold, whereby the connection end of the coupling element is bonded to the manifold.

Other attempts to provide injectors that mix two substances include devices that provide two hollow injection needles that are bonded together side-by-side. The relatively large thickness of the composite needle provides an enlarged distal aperture that may damage tissue upon insertion. In addition, adequate mixing of the two individual components is not guaranteed because the components emerge laterally, side-by-side from the distal end of the injection needles.

WO0069488A2 discloses an injector device for containers with an opening for an injection needle. The injector includes a housing, a seat or a carrier arranged to hold the needle and for allowing movement thereof in relation to the housing between a rear, needle-covering, position and a forward, needle exposing position. The injector has a penetration arrangement operable to move the needle from the rear position to the forward position, a return arrangement to move the needle in the rearward direction, and an injection arrangement to expel container content through the needle. The injector has a control button arranged on the housing that triggers the penetration arrangement and injection arrangement.

U.S. Pat. No. 4,026,288 discloses a syringe injecting device having a body with a slideway therein that receives a syringe carriage biased into one position by a spring and reciprocal in the slideway. A handle extends from the body and there is a communication between the carriage for the syringe and a gear in the handle. The gear is controlled by a latch having a detent which may be released by a trigger from permitting the carriage to be impelled forward under spring action to insert the needle of the syringe into a body.

In spite of the above advances, there remains a need for an applicator device that provides for the efficient administration of multiple and sequential injections of a substance including at least two components. There also remains a need for an applicator device for administering injections that enables a single puncture of a patient's skin to properly inject the two or more components that are mixed together. There is also a need for an applicator device that enables medical personnel to cover a broad area of tissue using multiple and sequential injections. In addition, there remains a need for an applicator device that may be easily re-filled with additional quantities of the two or more components. Moreover, there remains a need for an applicator device that is relatively inexpensive to manufacture, safe, and easy to use. There also remains a need for an applicator device having an injection needle that may be automatically extracted from the patient's skin without the need for the administrator to lift the device upward from the injected surface so that the device allows for multiple injections on a 2-D surface of a tissue while moving the device.

SUMMARY OF THE INVENTION

In one embodiment, a device for administering injections preferably includes at least one syringe barrel, at least one plunger connected with the at least one syringe barrel, a plunger base connected with the at least one plunger and is adapted for reciprocal movement along an axis, a needle housing adapted for reciprocal movement along the axis, the needle housing including at least one catch projecting from an outer surface thereof for selectively coupling the needle housing and the plunger base together for providing simultaneous movement of the needle housing and the plunger base in a first direction along the axis, and at least one catch actuator coupled with the at least one catch for selectively decoupling the needle housing from the plunger base so that the needle housing and the plunger base are capable of moving independently of one another along the axis.

In one embodiment, the device for administering injections desirably includes an injection actuator having gear teeth, a needle housing moveable along an axis and including an outer surface having a rack structure, the needle housing having an injection needle capable of moving from a retracted position to an extended position, at least one gear interconnecting the gear teeth of the injection actuator with the rack structure of the needle housing for advancing the needle housing along the axis, at least one syringe barrel, at least one plunger connected with the at least one syringe barrel, a plunger base connected with the at least one plunger and is adapted for reciprocal movement along an axis, at least one catch projecting from an outer surface of the needle housing for selectively coupling the needle housing and the plunger base together for providing simultaneous movement of the needle housing and the plunger base in a first direction along the axis, and at least one catch actuator coupled with the at least one catch for selectively decoupling the needle housing from the plunger base so that the needle housing and the plunger base are capable of moving independently of one another along the axis.

In one embodiment, a device for administering injections preferably includes a housing having an upper end, a lower end including a bottom surface with an injection needle opening, and an axis extending between the upper and lower ends of the housing, an injection needle disposed within the housing for moving along the axis between a retracted position in which the injection needle is disposed within the housing and an extended position in which a distal end of the injection needle extends through the injection needle opening at the bottom surface of the housing, a needle housing having the injection needle projecting therefrom and including an outer surface having a rack structure, a first syringe barrel and a first plunger connected therewith, a second syringe barrel and a second plunger connected therewith, a plunger base connected with the first and second plungers and being adapted for moving simultaneously with the first and second plungers, at least one conduit providing a fluid path between the first and second syringe barrels and the injection needle, at least one catch projecting from an outer surface of the needle housing for selectively coupling the needle housing and the plunger base together for providing simultaneous movement of the needle housing and the plunger base along the axis, at least one catch actuator coupled with the at least one catch for selectively decoupling the needle housing from the plunger base so that the needle housing and the plunger base are capable of moving independently of one another along the axis, a plunger spring in contact with the plunger base, whereby the plunger spring is compressible when the at least one catch of the needle housing is coupled with the plunger base for storing energy in the plunger spring, whereby the at least one catch is adapted for being decoupled from the plunger base by the at least one catch actuator when the needle housing is in the extended position so that the needle housing and the plunger base are capable of moving independently of one another and the energy stored in the plunger spring urges the plunger base to drive the first and second plungers into the respective first and second syringe barrels, and whereby the device is adapted to dispense a substance having at least two components when the injection needle is in the extended position.

In one embodiment, a device for administering injections desirably includes at least one reservoir containing a liquid component, at least one syringe barrel in fluid communication with the at least one reservoir, at least one plunger connected with the at least one syringe barrel and being moveable in a first direction for drawing the liquid component into the at least one syringe barrel, a plunger base connected with the at least one plunger, a needle housing adapted to be coupled with the plunger base for providing simultaneous movement of the needle housing, the plunger base, and the at least one plunger in the first direction, and an injection actuator being engageable with the needle housing via at least one gear for moving the needle housing in the first direction, whereby the device is adapted to allow automatic loading of the at least one syringe barrel with the liquid component.

In one embodiment, a device for administering injections preferably includes a housing having an upper end, a lower end including a bottom surface with an injection needle opening, and an axis extending between the upper and lower ends of the housing, an injection needle disposed within the housing for moving along the axis between a retracted position in which the injection needle is disposed within the housing and an extended position in which a distal end of the injection needle extends through the injection needle opening at the bottom surface of the housing, a first conduit for directing a first liquid component toward the injection needle, a second conduit for directing a second liquid component toward the injection needle, and an injection actuator coupled with the injection needle for moving the injection needle from the retracted position to the extended position and advancing the first and second liquid components toward the injection needle for dispensing a liquid solution including the first and second liquid components from the distal end of the injection needle.

In one embodiment, the device desirably includes a mixing chamber located between distal ends of the first and second conduits and a proximal end of the injection needle, the mixing chamber being adapted for combining the first and second liquid components into the liquid solution and directing the liquid solution into the proximal end of the needle.

In one embodiment, the device preferably includes an injection needle housing being adapted to hold the injection needle, the injection needle housing having an upper end and a lower end, whereby the distal end of the injection needle projects from the lower end of the injection needle housing, and whereby the injection actuator is coupled with the injection needle housing.

In one embodiment, the device desirably includes a needle hub connected with a proximal end of the injection needle for connecting the injection needle with the injection needle housing and directing the first and second liquid components toward the proximal end of the injection needle, whereby the needle hub includes the mixing chamber.

In one embodiment, the first conduit has a proximal end and a distal end in fluid communication with the mixing chamber, and the second conduit has a proximal end and a distal end in fluid communication with the mixing chamber.

In one embodiment, the device preferably includes a first reservoir in fluid communication with the proximal end of the first conduit for storing the first liquid component, and a second reservoir in fluid communication with the proximal end of the second conduit for storing the second liquid component.

In one embodiment, the device preferably includes a first syringe barrel in fluid communication with the first conduit, and a first plunger in the first barrel for alternatively drawing the first liquid component into the first barrel and dispensing the first liquid component from the first barrel and into the first conduit, a second syringe barrel in fluid communication with the second conduit, and a second plunger in the second barrel for alternatively drawing the second liquid component into the second barrel and dispensing the second liquid component from the second barrel and into the second conduit, and a plunger base moveable along the axis of the housing and being connected with the first and second plungers for ensuring simultaneous movement of the first and second plungers between the upper and lower ends of the housing so that the first and second liquid components are simultaneously drawn into and dispensed from the first and second syringe barrels.

In one embodiment, the first conduit preferably includes a first one-way check valve for directing flow of the first liquid component in a single downstream direction, the first one-way check valve including an upstream opening coupled with the first reservoir and a downstream opening, a first T-connector having a first opening in fluid communication with the downstream opening of the first one-way check valve, a second opening in fluid communication with the first syringe barrel, and a third opening, and a first tube having a proximal end in fluid communication with the third opening of the first T-connector and a downstream end in fluid communication with the injection needle, whereby the first liquid component flows between the first and second openings of the first T-connector as the first liquid component is drawn into the first syringe barrel and flows between the second and third openings of the first T-connector and into the proximal end of the first tube as the first liquid component is dispensed from the first syringe barrel.

In one embodiment, the second conduit preferably includes a second one-way check valve for directing flow of the second liquid component in a single downstream direction, the second one-way check valve including an upstream opening coupled with the second reservoir and a downstream opening, a second T-connector having a first opening in fluid communication with the downstream opening of the second one-way check valve, a second opening in fluid communication with the second syringe barrel, and a third opening, and a second tube having a proximal end in fluid communication with the third opening of the second T-connector and a downstream end in fluid communication with the injection needle, whereby the second liquid component flows between the first and second openings of the second T-connector as the second liquid component is drawn into the second syringe barrel and flows between the second and third openings of the second T-connector and into the proximal end of the second tube as the second liquid component is dispensed from the second syringe barrel.

In one embodiment, the device preferably includes at least one catch projecting from an outer surface of the needle housing for selectively coupling the needle housing and the plunger base together for providing simultaneous movement of the needle housing and the plunger base along the axis of the housing, and at least one catch actuator coupled with the at least one catch for selectively decoupling the needle housing from the plunger base so that the needle housing and the plunger base are capable of moving independently of one another along the axis of the housing.

In one embodiment, the device preferably includes a plunger spring having an upper end in contact with the plunger base and a lower end in contact with the housing, whereby the plunger spring is compressed when the at least one catch of the needle housing is coupled with the plunger base for storing energy in the plunger spring, and whereby the at least one catch is adapted for being decoupled from the plunger base so that the energy stored in the plunger spring urges the plunger base away from the bottom surface of the housing for driving the first and second plungers into the respective first and second syringe barrels as the plunger base moves away from the bottom surface of the housing.

In one embodiment, the injection actuator is preferably engageable for commencing an injection cycle that desirably includes a first stage during which the needle housing moves toward the lower end of the housing for advancing the distal end of the injection needle through the injection needle opening, with the at least one catch being coupled with the plunger base for pulling the plunger base toward the lower end of the housing for drawing the first and second liquid components into the first and second syringe barrels, and the plunger spring being compressed by the plunger base as the plunger base is pulled toward the lower end of the housing for storing energy in the plunger spring, and a second stage during which the at least one catch is decoupled from the plunger base so that the plunger base is free to move toward the upper end of the housing under the energy stored in the plunger spring while the distal end of the injection needle remains advanced through the injection needle opening, whereupon the first and second plungers are driven by the plunger base toward the upper end of the housing and into the first and second syringe barrels for dispensing the first and second liquid components from the first and second syringe barrels and supplying the first and second components to the injection needle.

In one embodiment, the plunger base desirably includes at least one slot and the needle housing includes at least one catch that forms a lost motion linkage with the at least one slot on the plunger base, and whereby the first stage of the injection cycle desirably has a first phase during which the at least one catch on the needle housing slides in the at least one slot of the plunger base as the needle housing moves toward the bottom surface of the housing and the plunger base remains stationary, and a second phase during which the at least one catch engages a closed end of the at least one slot on the plunger base for pulling the plunger base toward the bottom surface of the housing for drawing the first and second liquid components into the first and second syringe barrels and for storing energy in the plunger spring.

In one embodiment, the injection cycle preferably includes a third stage during which the needle housing moves toward the upper end of the housing for retracting the distal end of the injection needle through the injection needle opening and into the housing, and the at least one catch re-engages the plunger base for re-coupling the needle housing with the plunger base.

In one embodiment, the injection actuator is preferably coupled with the housing and is moveable between a first position and a second position, whereby the injection actuator is in the first position prior to the first stage of the injection cycle, is moveable from the first position to the second position during the first and second stages of the injection cycle, and is moveable from the second position back to the first position during the third stage of the injection cycle.

In one embodiment, the device preferably includes an actuator spring extending between an outer surface of the housing and the injection actuator for returning the actuator from the second position to the first position.

In one embodiment, the device preferably includes at least one one-way check valve in each of the first and second conduits for preventing the first and second liquid components from returning upstream. In one embodiment, the first conduit preferably includes a first tube and the second conduit preferably includes a second tube.

In one embodiment, a device for administering injections preferably includes a housing having an upper end, a lower end including a bottom surface with an injection needle opening, and an axis extending between the upper and lower ends of the housing, a needle housing disposed within the housing for moving along the axis, the needle housing having an upper end and a lower end with an injection needle projecting from the lower end of the needle housing, a first tube for directing a first liquid component into the injection needle, a second tube for directing a second liquid component into the injection needle, a first barrel in fluid communication with the first tube, and a first plunger in the first barrel for alternatively drawing the first liquid component into the first barrel and dispensing the first liquid component from the first barrel and into the first tube, a second barrel in fluid communication with the second tube, and a second plunger in the second barrel for alternatively drawing the second liquid components into the second barrel and dispensing the second liquid component from the second barrel and into the second tube, a plunger base moveable along the axis of the housing and being connected with the first and second plungers for ensuring simultaneous movement of the first and second plungers between the upper and lower ends of the housing so that the first and second liquid components are simultaneously drawn into and dispensed from the first and second barrels, and an injection actuator coupled with the needle housing for moving the injection needle toward the lower end of the housing for extending the injection needle through the injection needle opening and advancing the first and second liquid components toward the injection needle for dispensing a liquid solution including the first and second liquid components from a distal end of the injection needle.

In one embodiment, the device preferably includes a mixing chamber located within the needle housing between distal ends of the first and second tubes and a proximal end of the injection needle, the mixing chamber being adapted for combining the first and second liquid components into a liquid solution and directing the liquid solution into the proximal end of the injection needle.

In one embodiment, the device preferably includes at least one catch projecting from an outer surface of the needle housing for selectively coupling the needle housing with the plunger base for providing simultaneous movement of the needle housing and the plunger base along the axis of the housing, and at least one catch actuator coupled with the at least one catch for selectively decoupling the needle housing from the plunger base so that the needle housing and the plunger base are capable of moving independently of one another along the axis of the housing.

In one embodiment, the device desirably has a plunger spring having an upper end in contact with the plunger base and a lower end in contact with the housing, whereby the plunger spring is compressed when the at least one catch of the needle housing is coupled with the plunger base for storing energy in the plunger spring, and whereby the energy stored in the plunger spring urges the plunger base away from the bottom surface of the housing when the at least one catch is decoupled from the plunger base so that the plunger base drives the first and second plungers into the respective first and second barrels for dispensing the first and second liquid components from the first and second barrels.

In one embodiment, the injection actuator is preferably engageable for commencing an injection cycle including a first stage during which the needle housing moves toward the lower end of the housing for extending the distal end of the injection needle through the injection needle opening, with the at least one catch being coupled with the plunger base for pulling the plunger base toward the lower end of the housing for drawing the first and second liquid components into the first and second barrels, and the plunger spring being compressed by the plunger base as the plunger base is pulled toward the lower end of the housing for storing energy in the plunger spring, a second stage during which the at least one catch is decoupled from the plunger base so that the plunger base is free to move away from the needle housing and toward the upper end of the housing under the energy stored in the plunger spring for driving the first and second plungers toward the upper end of the housing and into the first and second barrels for dispensing the first and second liquid components from the first and second barrels, and a third stage during which the needle housing moves toward the upper end of the housing for retracting the distal end of the injection needle through the injection needle opening and into the housing, and the at least one catch re-engages the plunger base for re-coupling the needle housing with the plunger base.

In one embodiment, the device preferably includes at least one one-way check valve in each of the first and second tubes for preventing the first and second liquid components from returning upstream.

In one embodiment, a device for administering injections preferably includes a housing having an upper end, a lower end including a bottom surface having an injection needle opening, and an axis extending between the upper and lower ends, an injection needle disposed within the housing for moving along the axis between a retracted position in which the injection needle is disposed within the housing and an extended position in which a distal end of the injection needle extends through the injection needle opening at the bottom surface of the housing, a first barrel in fluid communication with the injection needle, a first plunger in the first barrel for alternatively drawing a first liquid component into the first barrel and dispensing the first liquid component from the first barrel and into the injection needle, a second barrel in fluid communication with the injection needle, a second plunger in the second barrel for alternatively drawing a second liquid component into the second barrel and dispensing the second liquid component from the second barrel and into the injection needle, a plunger base moveable along the axis of the housing and being connected with the first and second plungers for simultaneously moving the first and second plungers between the upper and lower ends of the housing so that the first and second liquid components are simultaneously drawn into and dispensed from the first and second barrels, and an injection actuator coupled with the injection needle for moving the injection needle from the retracted position to the extended position and dispensing the first and second liquid components from a distal end of the injection needle.

In one embodiment, the device desirably includes at least one catch projecting from an outer surface of the needle housing for selectively coupling the needle housing and the plunger base together for providing simultaneous movement of the needle housing and the plunger base along the axis of the housing during a first stage of an injection cycle, and at least one catch actuator coupled with the at least one catch for selectively decoupling the needle housing from the plunger base during a second stage of the injection cycle so that the needle housing and the plunger base are capable of moving independently of one another along the axis of the housing.

In one embodiment, the device preferably has a plunger spring having an upper end in contact with the plunger base and a lower end in contact with the housing, whereby the plunger spring is compressed when the at least one catch of the needle housing is coupled with the plunger base as the plunger base is pulled toward the lower end of the housing for storing energy in the plunger spring, and whereby when the at least one catch is decoupled from the plunger base the energy stored in the plunger spring urges the plunger base toward the upper end of the housing for driving the first and second plungers into the respective first and second barrels for dispensing the first and second liquid components from the first and second barrels.

In one embodiment, a device for administering injections includes a housing having an upper end, a lower end including a bottom surface with an injection needle opening, and an axis extending between the upper end and lower ends of the housing. The device preferably includes an injection needle disposed within the housing for moving along the axis between a retracted position in which the injection needle is disposed within the housing and an extended position in which a distal end of the injection needle extends through the injection needle opening at the bottom surface of the housing. The device desirably includes a first conduit for directing a first liquid component toward the injection needle, a second conduit for directing a second liquid component toward the injection needle, and a mixing chamber located between the distal ends of the first and second conduits and a proximal end of the injection needle. In one embodiment, the first conduit preferably includes a first tube and the second conduit preferably includes a second tube. The mixing chamber is desirably adapted for combining the first and second liquid components into a liquid solution and directing the liquid solution into the proximal end of the needle. In one embodiment, the device desirably includes an injection actuator coupled with the injection needle for moving the injection needle from the retracted position to the extended position and advancing the first and second liquid components toward the mixing chamber for dispensing the liquid solution from the distal end of the injection needle.

In one embodiment, the device preferably includes an injection needle housing being adapted to hold the injection needle. The injection needle housing desirably has an upper end and a lower end, whereby the distal end of the injection needle projects from the lower end of the injection needle housing. In one embodiment, the injection actuator is preferably coupled with the injection needle housing.

In one embodiment, the device desirably includes a needle hub connected with a proximal end of the injection needle. The needle hub is preferably adapted for connecting the injection needle with the injection needle housing and for directing the first and second liquid components from the first and second conduits toward the proximal end of the injection needle. In one embodiment, the needle hub preferably includes the mixing chamber for combining the first and second liquid components.

In one embodiment, the first conduit preferably has a proximal end and a distal end that is in fluid communication with the mixing chamber. The second conduit also desirably has a proximal end and a distal end that is in fluid communication with the mixing chamber. The device preferably includes a first reservoir, such as a first vial, in fluid communication with the proximal end of the first conduit for storing the first liquid component, and a second reservoir, such as a second vial, in fluid communication with the proximal end of the second conduit for storing the second liquid component.

In one embodiment, the device preferably includes a first barrel in fluid communication with the first conduit, and a first plunger in the first barrel for alternatively drawing the first liquid component into the first barrel and dispensing the first liquid component from the first barrel and into the first conduit. In one embodiment, the first liquid component is drawn into the first barrel as the first the plunger is pulled toward a lower end of the housing, and is dispensed from the first barrel as the first plunger is driven toward the upper end of the housing. The device preferably includes a second barrel in fluid communication with the second conduit, and a second plunger in the second barrel for alternatively drawing the second liquid component into the second barrel and dispensing the second liquid from the second barrel and into the second conduit. In one embodiment, the second liquid component is drawn into the second barrel as the second plunger moves toward the lower end of the housing, and is dispensed from the second barrel as the second plunger moves toward the upper end of the housing.

In one embodiment, the device preferably includes a plunger base movable along the axis of the housing between the upper and lower ends thereof. The plunger base is preferably connected with the first and second barrels for insuring simultaneous movement of the first and second barrels between the upper and lower ends of the housing. As a result, the first and second components are simultaneously drawn into and dispensed from the respective first and second barrels.

In one embodiment, the first conduit preferably includes a first one-way check valve for directing flow of the first liquid component in a single downstream direction, the first one-way check valve including an upstream opening coupled with the first reservoir and a downstream opening. The first conduit desirably has a first T-connector having a first opening in fluid communication with the downstream opening of the first one-way check valve, a second opening in fluid communication with the first syringe barrel, and a third opening. The first conduit may include a first tube having a proximal end in fluid communication with the third opening of the first T-connector and a downstream end in fluid communication with the injection needle. In one embodiment, the first liquid component desirably flows between the first and second openings of the first T-connector as the first liquid component is drawn into the first syringe barrel and flows between the second and third openings of the first T-connector and into the proximal end of the first tube as the first liquid component is dispensed from the first syringe barrel.

In one embodiment, the second conduit preferably includes a second one-way check valve for directing flow of the second liquid component in a single downstream direction, the second one-way check valve including an upstream opening coupled with the second reservoir and a downstream opening. The second conduit desirably has a second T-connector having a first opening in fluid communication with the downstream opening of the second one-way check valve, a second opening in fluid communication with the second syringe barrel, and a third opening. The second conduit may include a second tube having a proximal end in fluid communication with the third opening of the second T-connector and a downstream end in fluid communication with the injection needle. In one embodiment, the second liquid component flows between the first and second openings of the second T-connector as the second liquid component is drawn into the second syringe barrel and flows between the second and third openings of the second T-connector and into the proximal end of the second tube as the second liquid component is dispensed from the second syringe barrel.

In one embodiment, the device preferably includes at least one catch projecting from an outer surface of the needle housing for selectively coupling the needle housing and the plunger base together so as to provide for simultaneous movement of the needle housing and the plunger base along the axis of the housing. In one embodiment, the coupling between the needle housing and the plunger base only occurs during selected stages of an injection cycle. The device preferably includes at least one catch actuator coupled with the at least catch for selectively decoupling the needle housing from the plunger base so that the needle housing and the plunger base are capable of moving independently of one another along the axis of the housing.

In one embodiment, the at least one catch on the needle housing preferably includes a pair of catches projecting outwardly from an upper end of the needle housing. In one embodiment, as the needle housing is moved in a downward direction by the injection actuator, the at least one catch engages one or more inner surfaces of the housing for activating the at least one catch. In one embodiment, the at least one catch is activated by being retracted into the needle housing. As the at least one catch retracts inside the needle housing, the at least one catch disengages from the plunger base so that the needle housing and the plunger base are no longer coupled together and may move independently of one another along the axis of the housing.

In one embodiment, the device includes a plunger spring having an upper end in contact with the plunger base and a lower end in contact with the housing. In one embodiment, the plunger spring is preferably compressed when the at least one catch of the needle housing is coupled with the plunger base for storing energy in the plunger spring. The at least one catch is desirably adapted for being decoupled from the plunger base so that the energy stored in the plunger spring urges the plunger base away from the bottom surface of the housing for driving the first and second plungers into the respective first and second barrels as the plunger base moves away from the bottom surface of the housing.

In one embodiment, the injection actuator is engageable for commencing an injection cycle. In one embodiment, the injection actuator is a handle or trigger that is connected to an outer surface of the housing and may be engaged by an operator. In one embodiment, the injection actuator is pressed, preferably towards the housing, for commencing an injection cycle and is released and returned to the original position under the force of a return spring. In one embodiment, an injection cycle includes a first stage during which the needle housing moves toward the lower end of the housing for advancing the distal end of the injection needle through the injection needle opening. In addition, the first stage preferably includes the at least one catch being coupled with the plunger base for pulling the plunger base toward the lower end of the housing for drawing the first and second liquid components into the first and second barrels. As the plunger base is initially pulled toward the lower end of the housing by the needle housing, the plunger spring is compressed by the plunger base for storing energy in the plunger spring.

In one embodiment, the injection cycle preferably includes a second stage during which the at least one catch on the needle housing is decoupled from the plunger base so that the plunger base is free to move toward the upper end of the housing under the energy stored in the plunger spring, while the distal end of the injection needle remains advanced through the injection needle opening. After the plunger base has been decoupled from the needle housing, the first and second plungers are preferably driven by the plunger base toward the upper end of the housing and into the first and second barrels for dispensing the first and second liquid components from the first and second barrels.

In one embodiment, the plunger base desirably includes at least one slot and the needle housing desirably has at least one catch that forms a lost motion linkage with the at least one slot on the plunger base. In one embodiment, the first stage of the injection cycle preferably includes a first phase during which the at least one catch on the needle housing slides in the at least one slot of the plunger base as the needle housing moves toward the bottom surface of the device housing and the plunger base remains stationary, and a second phase during which the at least one catch engages a closed end of the at least one slot on the plunger base for pulling the plunger base toward the bottom surface of the device housing for drawing the first and second liquid components into the first and second syringe barrels and for storing energy in the plunger spring.

In one embodiment, an injection cycle preferably includes a third stage during which the needle housing moves toward the upper end of the housing for retracting the distal end of the injection needle through the injection needle opening and into the housing. As the needle housing moves in an upward direction, the at least one catch actuator projecting from the needle housing preferably re-engages the plunger base for re-coupling the needle housing with the plunger base.

In one embodiment, the injection actuator is desirably coupled with the housing and is movable between a first position and a second position. In one embodiment, the injection actuator is preferably in the first position prior to the commencement of the first stage of the injection cycle, is movable from the first position to the second position during the first and second stages of the injection cycle, and is movable from the second position back to the initial first position during the third stage of the injection cycle. In one embodiment, the injection actuator is uncompressed in the first position and fully compressed in the second position. The injection actuator may include a handle or a trigger.

In one embodiment, the device preferably includes at least one one-way check valve in each of the first and second conduits for preventing the first and second liquid components from returning upstream to the first and second reservoirs after the first and second liquid components have been drawn into the first and second barrels. In one embodiment, the first conduit includes a first tube and the second conduit includes a second tube. In one embodiment, the device includes a first vial storing the first liquid component and a second vial storing the second liquid component. The first and second vials desirably include multiple doses of each of the first and second liquid components. As such, after the first and second liquid components have been drawn from the respective first and second vials, it is undesirable for the previously drawn first and second liquid components to be returned to the first and second vials, which may contaminate the components stored therein.

In one embodiment, a device for administering injections preferably includes a housing having an upper end, a lower end including a bottom surface with an injection needle opening, and an axis extending between the upper and lower ends of the housing. The device preferably includes an injection needle housing disposed within the housing for moving along the axis, the injection needle housing preferably having an upper end and a lower end with an injection needle projecting from the lower end of the injection needle housing. The device preferably includes a first conduit for directing a first liquid component into the needle housing, a second conduit for directing a second liquid component into the needle housing, and a mixing chamber located within the injection needle housing between distal ends of the first and second conduits and a proximal end of the injection needle. The mixing chamber is preferably adapted for combining the first and second liquid components into a liquid solution and directing the liquid solution into the proximal end of the injection needle for injection into a patient.

In one embodiment, the device preferably includes a first barrel in fluid communication with the first conduit, and a first plunger in the first barrel alternatively drawing the first liquid component into the first barrel and dispensing the first liquid component from the first barrel and into the first conduit. The device desirably includes a second barrel in fluid communication with the second conduit, and a second plunger in the second barrel for alternatively drawing the second liquid component into the second barrel and dispensing the second liquid component from the second barrel and into the second conduit. In one embodiment, the device preferably includes a plunger base movable along the axis of the housing and being connected with the first and second barrels for ensuring simultaneous movement of the first and second plungers between the upper and lower ends of the housing so that the first and second liquid components are simultaneously drawn into and dispensed from the first and second barrels. The device preferably includes an injection actuator coupled with the injection needle for moving the injection needle housing toward the lower end of the housing for extending the injection needle through the injection needle opening and advancing the first and second liquid components toward the mixing chamber for dispensing the liquid solution from a distal end of the injection needle.

In one embodiment, the device desirably includes at least one catch projecting from an outer surface of the needle housing for selectively coupling the needle housing with the plunger base so as to provide for simultaneous movement of the needle housing and the plunger base along the axis of the housing. The device desirably includes at least one catch actuator coupled with the at least one catch for selectively decoupling the needle housing from the plunger base so that the needle housing and the plunger base are capable of moving independently of one another along the axis of the housing.

In one embodiment, the device desirably includes a plunger spring having an upper end in contact with the plunger base and a lower end in contact with the housing. In one embodiment, the plunger spring is preferably compressed when the at least one catch of the needle housing is coupled with the plunger base for storing energy in the plunger spring. In one embodiment, the energy stored in the plunger spring preferably urges the plunger base away from the bottom surface of the housing when the at least one catch has been decoupled from the plunger base so that the plunger base drives the first and second plungers into the respective first and second barrels for dispensing the first and second liquid components from the first and second barrels.

In one embodiment, the injection actuator is preferably engageable for commencing an injection cycle including at least a first stage, a second stage, and a third stage. In one embodiment, the injection cycle desirably includes the first stage during which the needle housing moves toward the lower end of the housing for extending the distal end of the injection needle through the injection needle opening, with the at least one catch actuator being coupled with the plunger base for pulling the plunger base toward the lower end of the housing for drawing the first and second liquid components into the first and second barrels. During this stage, the plunger spring is preferably compressed by the plunger base as the plunger base is pulled toward the lower end of the housing for storing energy in the plunger spring.

In one embodiment, the second stage of the injection cycle preferably includes decoupling the at least one catch from the plunger base so that the plunger base is free to move away from the needle housing and toward the upper end of the housing under the energy stored in the plunger spring so as to drive the first and second plungers toward the upper end of the housing and into the first and second barrels for dispensing the first and second liquid components from the first and second barrels.

In one embodiment, the injection cycle preferably includes the third stage during which the needle housing moves toward the upper end of the housing for retracting the distal end of the injection needle through the injection needle opening and into the housing. During the third stage, the at least one catch actuator preferably re-engages the plunger base for re-coupling the needle housing with the plunger base for another injection cycle.

In one embodiment, a device for administering injections preferably includes a housing having an upper end, a lower end including a bottom surface having an injection needle opening, and an axis extending between the upper and lower ends. The device desirably includes an injection needle disposed within the housing for moving along the axis between a retracted position in which the injection needle is disposed within the housing and an extended position in which a distal end of the injection needle extends through the injection needle opening at the bottom surface of the housing. In one embodiment, the device preferably includes a first barrel in fluid communication with the injection needle, a first plunger in the first barrel for alternatively drawing a first liquid component into the first barrel and dispensing the first liquid component from the first barrel and into the injection needle, a second barrel in fluid communication with the injection needle, and a second plunger in the second barrel for alternatively drawing a second liquid component into the second barrel and dispensing the second liquid component from the second barrel into the injection needle. In one embodiment, the device preferably includes a plunger base that is movable along the axis of the housing and is connected with the first and second plungers for simultaneously moving the first and second plungers between the upper and lower ends of the housing so that the first and second liquid components are simultaneously drawn into and dispensed from the first and second barrels. The device desirably includes an injection actuator coupled with the injection needles for moving the injection needle from the retracted position to the extended position and for dispensing the first and second liquid components from a distal end of the injection needle.

In one embodiment, a device for administering injections preferably includes a housing having an upper end, a lower end including a bottom surface with an injection needle opening, and an axis extending between the upper and lower ends of the housing; an injection needle disposed within the housing for moving along the axis between a retracted position in which the injection needle is disposed within the housing and an extended position in which a distal end of the injection needle extends through the injection needle opening at the bottom surface of the housing; a first conduit for directing a first liquid component toward the injection needle; a second conduit for directing a second liquid component toward the injection needle; a mixing chamber located between distal ends of the first and second conduits and a proximal end of the injection needle, the mixing chamber being adapted for combining the first and second liquid components into a liquid solution and directing the liquid solution into the proximal end of the needle; and an injection actuator coupled with the injection needle for moving the injection needle from the retracted position to the extended position and advancing the first and second liquid components toward the mixing chamber for dispensing the liquid solution from the distal end of the injection needle.

In one embodiment, the device preferably includes an injection needle housing being adapted to hold the injection needle, the injection needle housing having an upper end and a lower end, wherein the distal end of the injection needle projects from the lower end of the injection needle housing, and wherein the injection actuator is coupled with the injection needle housing.

In one embodiment, the device preferably includes a needle hub connected with a proximal end of the injection needle for connecting the injection needle with the injection needle housing and directing the first and second liquid components toward the proximal end of the injection needle, wherein the needle hub includes the mixing chamber.

In one embodiment, the first conduit preferably has a proximal end and a distal end in fluid communication with the mixing chamber, and the second conduit has a proximal end and a distal end in fluid communication with the mixing chamber.

In one embodiment, the housing preferably includes a first reservoir in fluid communication with the proximal end of the first conduit for storing the first liquid component; and a second reservoir in fluid communication with the proximal end of the second conduit for storing the second liquid component.

In one embodiment, the device preferably includes a first syringe barrel in fluid communication with the first conduit, and a first plunger in the first barrel for alternatively drawing the first liquid component into the first barrel and dispensing the first liquid component from the first barrel and into the first conduit; a second syringe barrel in fluid communication with the second conduit, and a second plunger in the second barrel for alternatively drawing the second liquid component into the second barrel and dispensing the second liquid component from the second barrel and into the second conduit; and a plunger base moveable along the axis of the housing and being connected with the first and second plungers for ensuring simultaneous movement of the first and second plungers between the upper and lower ends of the housing so that the first and second components are simultaneously drawn into and dispensed from the first and second syringe barrels.

In one embodiment, the first conduit preferably includes a first one-way check valve for directing flow of the first liquid component in a single downstream direction, the first one-way check valve including an upstream opening coupled with the first reservoir and a downstream opening, a first T-connector having a first opening in fluid communication with the downstream opening of the first one-way check valve, a second opening in fluid communication with the first syringe barrel, and a third opening, and a first tube having a proximal end in fluid communication with the third opening of the first T-connector and a downstream end in fluid communication with the injection needle, wherein the first liquid component flows between the first and second openings of the first T-connector as the first liquid component is drawn into the first syringe barrel and flows between the second and third openings of the first T-connector and into the proximal end of the first tube as the first liquid component is dispensed from the first syringe barrel.

In one embodiment, the second conduit preferably includes a second one-way check valve for directing flow of the second liquid component in a single downstream direction, the second one-way check valve including an upstream opening coupled with the second reservoir and a downstream opening, a second T-connector having a first opening in fluid communication with the downstream opening of the second one-way check valve, a second opening in fluid communication with the second syringe barrel, and a third opening, and a second tube having a proximal end in fluid communication with the third opening of the second T-connector and a downstream end in fluid communication with the injection needle, wherein the second liquid component flows between the first and second openings of the second T-connector as the second liquid component is drawn into the second syringe barrel and flows between the second and third openings of the second T-connector and into the proximal end of the second tube as the second liquid component is dispensed from the second syringe barrel.

In one embodiment, the device preferably includes at least one catch projecting from an outer surface of the needle housing for selectively coupling the needle housing and the plunger base together for providing simultaneous movement of the needle housing and the plunger base along the axis of the housing; and at least one catch actuator coupled with the at least one catch for selectively decoupling the needle housing from the plunger base so that the needle housing and the plunger base are capable of moving independently of one another along the axis of the housing.

In one embodiment, the device preferably includes a plunger spring having an upper end in contact with the plunger base and a lower end in contact with the housing, wherein the plunger spring is compressed when the at least one catch of the needle housing is coupled with the plunger base for storing energy in the plunger spring, and wherein the at least one catch is adapted for being decoupled from the plunger base so that the energy stored in the plunger spring urges the plunger base away from the bottom surface of the housing for driving the first and second plungers into the respective first and second syringe barrels as the plunger base moves away from the bottom surface of the housing.

In one embodiment, the injection actuator is preferably engageable for commencing an injection cycle including a first stage during which the needle housing moves toward the lower end of the housing for advancing the distal end of the injection needle through the injection needle opening, with the at least one catch actuator being coupled with the plunger base for pulling the plunger base toward the lower end of the housing for drawing the first and second liquid components into the first and second syringe barrels, and the plunger spring being compressed by the plunger base as the plunger base is pulled toward the lower end of the housing for storing energy in the plunger spring; and a second stage during which the at least one catch is decoupled from the plunger base so that the plunger base is free to move toward the upper end of the housing under the energy stored in the plunger spring while the distal end of the injection needle remains advanced through the injection needle opening, whereupon the first and second plungers are driven by the plunger base toward the upper end of the housing and into the first and second syringe barrels for dispensing the first and second liquid components from the first and second syringe barrels and supplying the first and second components to the injection needle.

In one embodiment, the plunger base preferably includes at least one slot and the needle housing comprises at least one catch that forms a lost motion linkage with the at least one slot on the plunger base. The first stage of the injection cycle preferably includes a first phase during which the at least one catch on the needle housing slides in the at least one slot of the plunger base as the needle housing moves toward the bottom surface of the device housing and the plunger base remains stationary, and a second phase during which the at least one catch engages a closed end of the at least one slot on the plunger base for pulling the plunger base toward the bottom surface of the device housing for drawing the first and second liquid components into the first and second syringe barrels and for storing energy in the plunger spring.

In one embodiment, the injection cycle preferably further includes a third stage during which the needle housing moves toward the upper end of the housing for retracting the distal end of the injection needle through the injection needle opening and into the housing, and the at least one catch actuator re-engages the plunger base for re-coupling the needle housing with the plunger base.

In one embodiment, the injection actuator is preferably coupled with the housing and is moveable between a first position and a second position, wherein the injection actuator is in the first position prior to the first stage of the injection cycle, is moveable from the first position to the second position during the first and second stages of the injection cycle, and is moveable from the second position back to the first position during the third stage of the injection cycle.

In one embodiment, the device preferably includes an actuator spring extending between an outer surface of the housing and the injection actuator for returning the actuator from the second position to the first position.

In one embodiment, the device preferably includes at least one one-way check valve in each of the first and second conduits for preventing the first and second liquid components from returning upstream.

In one embodiment, the first conduit preferably includes a first tube and the second conduit preferably includes a second tube.

In one embodiment, a device for administering injections preferably includes a device housing having an upper end, a lower end including a bottom surface with an injection needle opening, and an axis extending between the upper and lower ends of the housing; a needle housing disposed within the device housing for moving along the axis, the needle housing having an upper end and a lower end with an injection needle projecting from the lower end of the needle housing; a first tube for directing a first liquid component into the injection needle; a second tube for directing a second liquid component into the injection needle; a mixing chamber located within the needle housing between distal ends of the first and second tubes and a proximal end of the injection needle, the mixing chamber being adapted for combining the first and second liquid components into a liquid solution and directing the liquid solution into the proximal end of the injection needle; a first barrel in fluid communication with the first tube, and a first plunger in the first barrel for alternatively drawing the first liquid component into the first barrel and dispensing the first liquid component from the first barrel and into the first tube; a second barrel in fluid communication with the second tube, and a second plunger in the second barrel for alternatively drawing the second liquid components into the second barrel and dispensing the second liquid component from the second barrel and into the second tube; a plunger base moveable along the axis of the housing and being connected with the first and second plungers for ensuring simultaneous movement of the first and second plungers between the upper and lower ends of the housing so that the first and second liquid components are simultaneously drawn into and dispensed from the first and second barrels; and an injection actuator coupled with the injection needle housing for moving the injection needle toward the lower end of the housing for extending the injection needle through the injection needle opening and advancing the first and second liquid components toward the mixing chamber for dispensing the liquid solution from a distal end of the injection needle.

In one embodiment, the device preferably includes at least one catch projecting from an outer surface of the needle housing for selectively coupling the needle housing with the plunger base for providing simultaneous movement of the needle housing and the plunger base along the axis of the housing; and at least one catch actuator coupled with the at least one catch for selectively decoupling the needle housing from the plunger base so that the needle housing and the plunger base are capable of moving independently of one another along the axis of the housing.

In one embodiment, the device preferably includes a plunger spring having an upper end in contact with the plunger base and a lower end in contact with the housing, wherein the plunger spring is compressed when the at least one catch of the needle housing is coupled with the plunger base for storing energy in the plunger spring, wherein the energy stored in the plunger spring urges the plunger base away from the bottom surface of the housing when the at least one catch is decoupled from the plunger base so that the plunger base drives the first and second plungers into the respective first and second barrels for dispensing the first and second liquid components from the first and second barrels.

In one embodiment, the injection actuator is preferably engageable for commencing an injection cycle including a first stage during which the needle housing moves toward the lower end of the device housing for extending the distal end of the injection needle through the injection needle opening, with the at least one catch actuator being coupled with the plunger base for pulling the plunger base toward the lower end of the housing for drawing the first and second liquid components into the first and second barrels, and the plunger spring being compressed by the plunger base as the plunger base is pulled toward the lower end of the device housing for storing energy in the plunger spring; a second stage during which the at least one catch is decoupled from the plunger base so that the plunger base is free to move away from the needle housing and toward the upper end of the device housing under the energy stored in the plunger spring for driving the first and second plungers toward the upper end of the housing and into the first and second barrels for dispensing the first and second liquid components from the first and second barrels; and a third stage during which the needle housing moves toward the upper end of the device housing for retracting the distal end of the injection needle through the injection needle opening and into the device housing, and the at least one catch actuator re-engages the plunger base for re-coupling the needle housing with the plunger base.

In one embodiment, the device preferably includes at least one one-way check valve in each of the first and second tubes for preventing the first and second liquid components from returning upstream.

In one embodiment, a device for administering injections preferably includes a housing having an upper end, a lower end including a bottom surface having an injection needle opening, and an axis extending between the upper and lower ends; an injection needle disposed within the housing for moving along the axis between a retracted position in which the injection needle is disposed within the housing and an extended position in which a distal end of the injection needle extends through the injection needle opening at the bottom surface of the housing; a first barrel in fluid communication with the injection needle; a first plunger in the first barrel for alternatively drawing a first liquid component into the first barrel and dispensing the first liquid component from the first barrel and into the injection needle; a second barrel in fluid communication with the injection needle; a second plunger in the second barrel for alternatively drawing a second liquid component into the second barrel and dispensing the second liquid component from the second barrel and into the injection needle; a plunger base moveable along the axis of the housing and being connected with the first and second plungers for simultaneously moving the first and second plungers between the upper and lower ends of the housing so that the first and second liquid components are simultaneously drawn into and dispensed from the first and second barrels; and an injection actuator coupled with the injection needle for moving the injection needle from the retracted position to the extended position and dispensing the first and second liquid components from a distal end of the injection needle.

In one embodiment, the device preferably includes at least one catch projecting from an outer surface of the needle housing for selectively coupling the needle housing and the plunger base together for providing simultaneous movement of the needle housing and the plunger base along the axis of the housing during a first stage of an injection cycle; and at least one catch actuator coupled with the at least one catch for selectively decoupling the needle housing from the plunger base during a second stage of the injection cycle so that the needle housing and the plunger base are capable of moving independently of one another along the axis of the housing.

In one embodiment, the device preferably includes a plunger spring having an upper end in contact with the plunger base and a lower end in contact with the housing, wherein the plunger spring is compressed when the at least one catch of the needle housing is coupled with the plunger base as the plunger base is pulled toward the lower end of the housing for storing energy in the plunger spring, wherein when the at least one catch is decoupled from the plunger base the energy stored in the plunger spring urges the plunger base toward the upper end of the housing for driving the first and second plungers into the respective first and second barrels for dispensing the first and second liquid components from the first and second barrels.

These and other preferred embodiments of the present invention will be described in more detail below.

BRIEF DESCRIPTION OF THE DRAWING

FIGS. 4A-4G show various views of a section of the injection system for an applicator shown in FIG. 3.

FIG. 6A shows a front elevational view of an upper end of a needle housing having catches in an extended position, in accordance with one embodiment of the present invention.

FIG. 6B shows the needle housing of FIG. 6A with the catches in a retracted position.

FIGS. 7A-7B show a method of actuating catches on a needle housing, in accordance with one embodiment of the present invention.

DETAILED DESCRIPTION

Figure 1A:
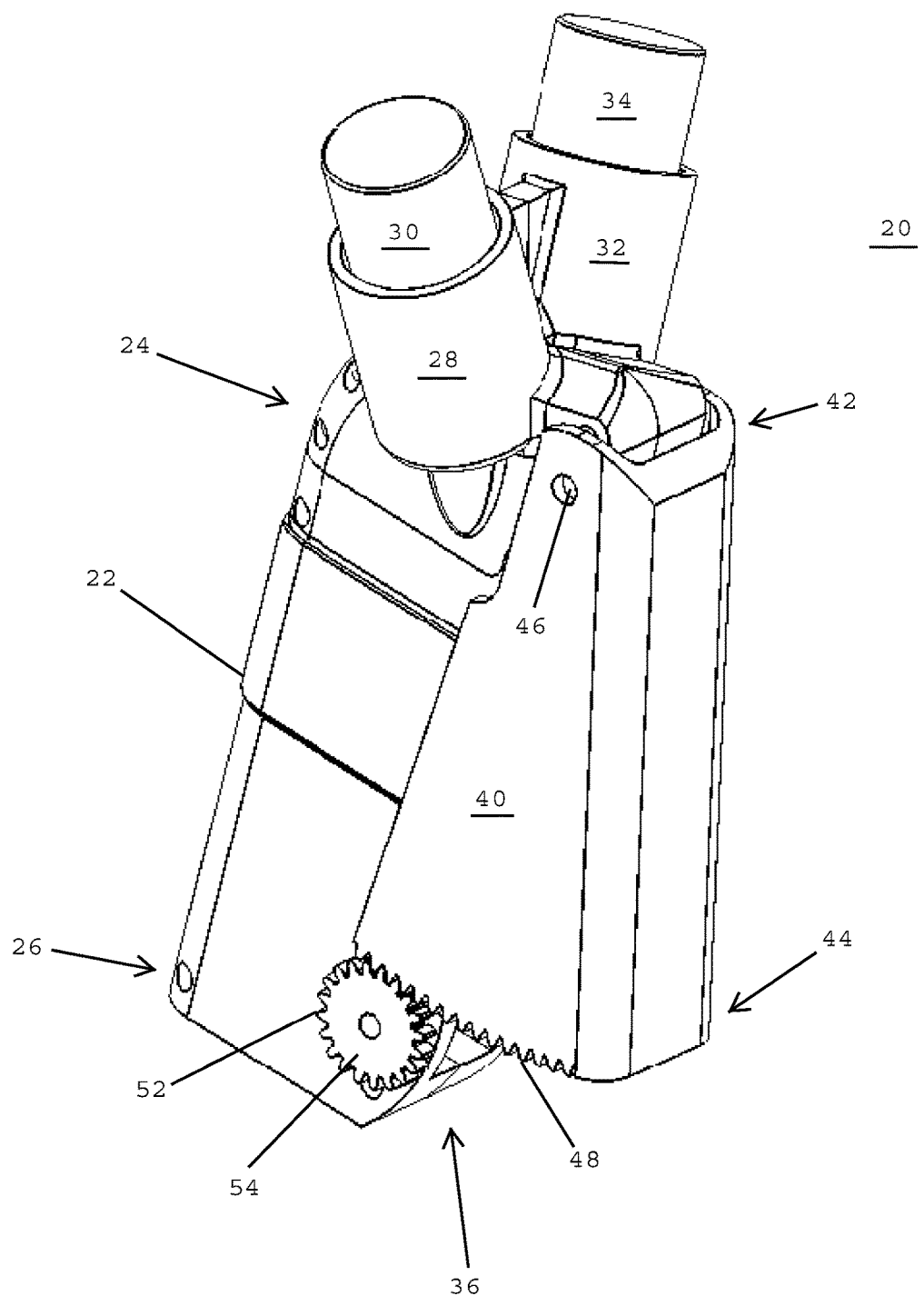
FIGS. 1A-1C show an applicator device for administering injections, in accordance with one embodiment of the present invention.

Referring to FIG. 1A, in one embodiment of the present invention, an applicator device 20 for administering injections preferably includes a housing 22 having an upper end 24 and a lower end 26. In one embodiment, the upper end 24 of the housing 22 preferably includes a first vial holder 28 adapted to receive a first vial 30 containing a first component, such as a first liquid component, and a second vial holder 32 adapted to receive a second vial 34 containing a second component, such as a second liquid component. The first and second vial holders 28, 32 may be adapted to receive replacement vials so that the first and second vials 30, 34 may be removed when empty and replaced with the replacement vials.

Figure 3:
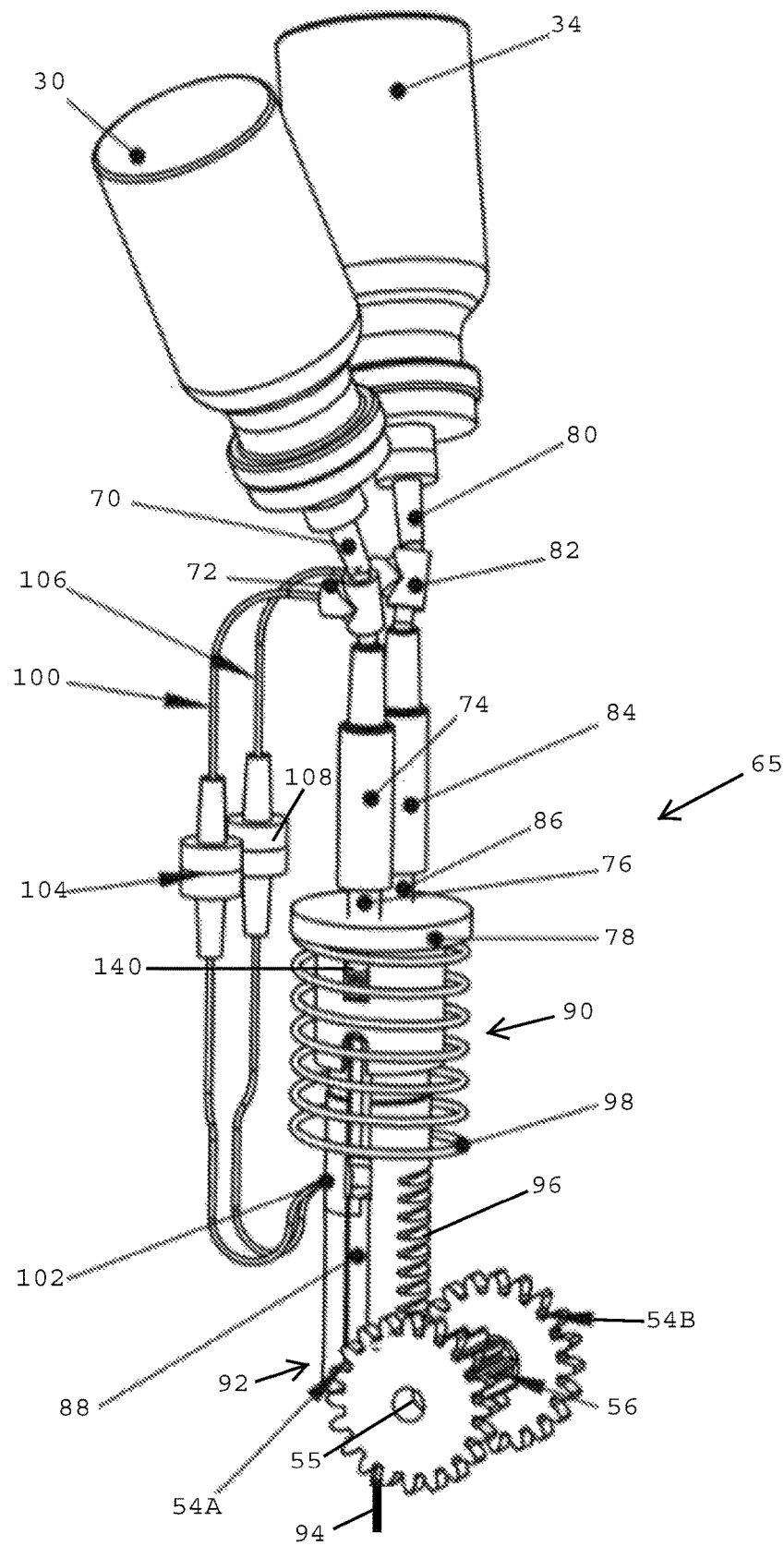
FIG. 3 shows a drive system and an injection system for the applicator device shown in FIGS. 1A-1C and 2.

In one embodiment, the applicator device 20 preferably includes a drive system 36 for advancing an injection needle (not shown) from the lower end 26 of the housing 22 for insertion into a tissue. In one embodiment, the first and second components are drawn from the first and second vials 30, 34, advanced downstream toward the injection needle, mixed together, and dispensed from the injection needle into the tissue. In one embodiment, the mixing of the two components occurs once the two components exit the first and second tubes 100, 106 (FIG. 3). Although the embodiment shown in FIG. 1A includes two vials containing two different components, in other embodiments the applicator device 20 may be adapted to receive three or more vials containing three or more components that are mixed together for formulating a mixed, injectable solution.

In one embodiment, the drive system 36 preferably includes an injection actuator, such as a handle 40, having an upper end 42 and a lower end 44. The upper end 42 of the handle 40 may be pivotally coupled with the upper end 24 of the housing 22 via a pivot connection 46. In one embodiment, the handle may be pressed toward the housing 22 for activating the drive system 36. The lower end 44 of the handle 40 desirably includes at least one set of gear teeth 48 that desirably engage gear teeth 52 on at least one external gear 54 that is rotatably mounted at the lower end 26 of the housing 22. In one embodiment, the handle 40 desirably has a C-shaped cross-section that conforms to the outer surface of the housing 22.

Figure 1C:
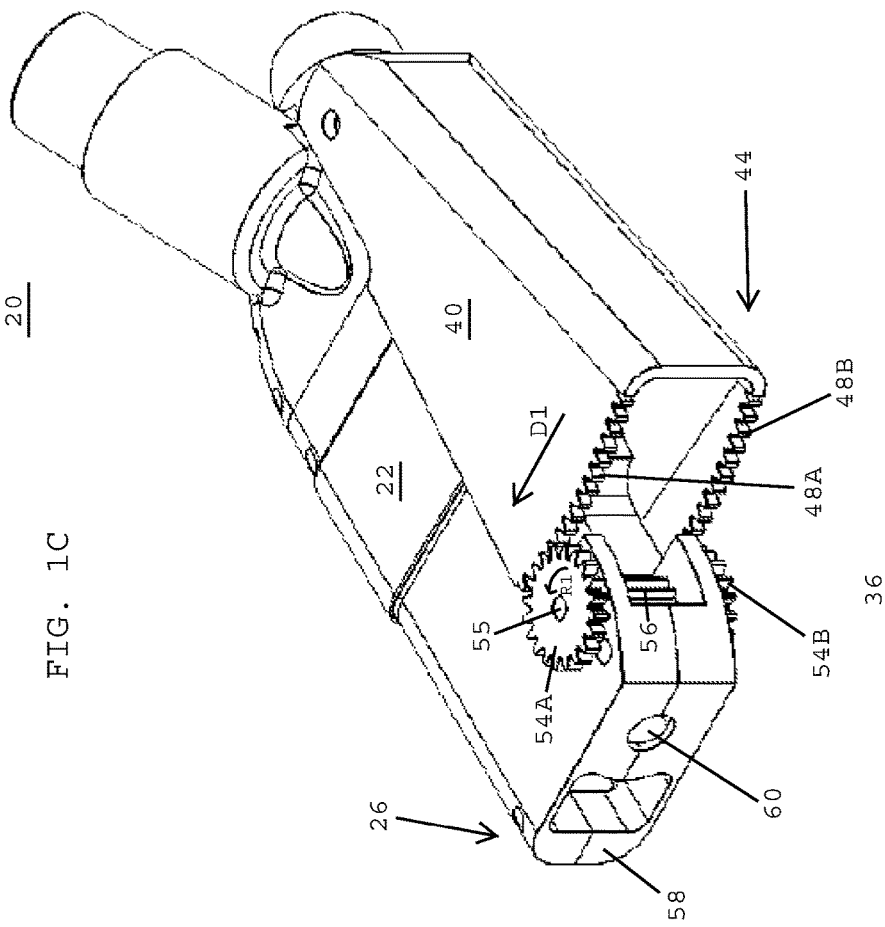
Figure 1B:
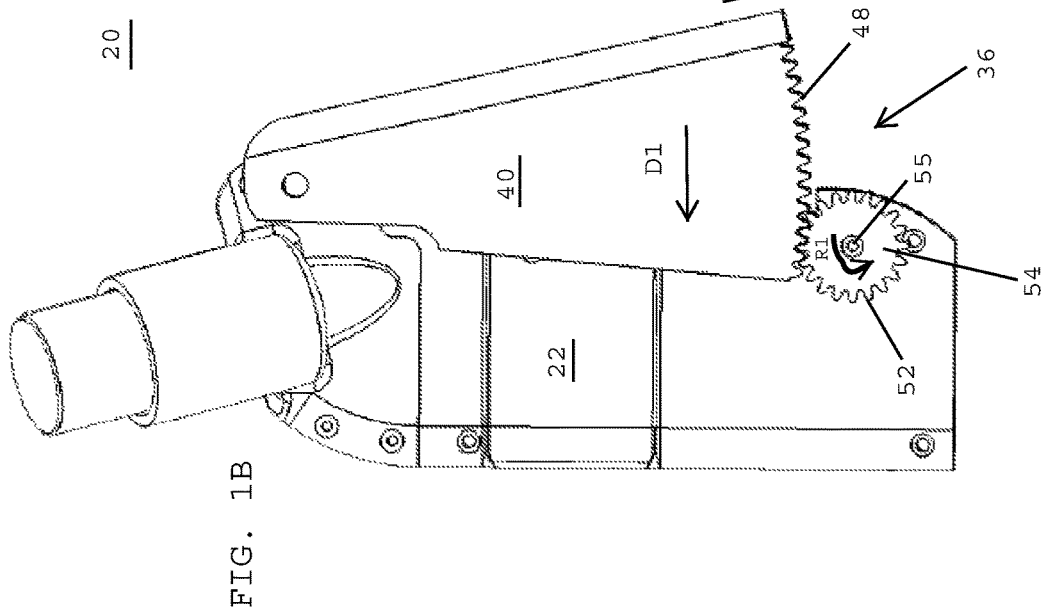

Referring to FIG. 1B, in one embodiment, the handle 40 may be pressed toward the housing 22 in the direction indicated $D_1$ for activating the drive system 36 of the applicator device 20. As the handle 40 is pressed in the direction $D_1$, the gear teeth 48 at the lower end 44 of the handle 40 preferably engage the gear teeth 52 on the external gear 54 for rotating the external gear 54 in a counterclockwise direction indicated $R_1$.

Referring to FIG. 1C, in one embodiment, the drive system 36 of the applicator device 20 preferably includes a first external gear 54A rotatably mounted on a first side of the housing 22 and a second external gear 54B rotatably mounted on a second side of the housing 22. In one embodiment, the handle 40 desirably includes a first set of gear teeth 48A at a lower end of the handle that are adapted to mesh with the gear teeth of the first external gear 54A and a second set of gear teeth 48B at a lower end of the handle adapted to mesh with the gear teeth on the second external gear 54B. In one embodiment, the first and second external gears 54A, 54B rotate in a first direction as the handle is pressed toward the device housing 22, and a second, opposite direction as the handle returns to the original position shown in FIGS. 1A-1C.

Figure 10:
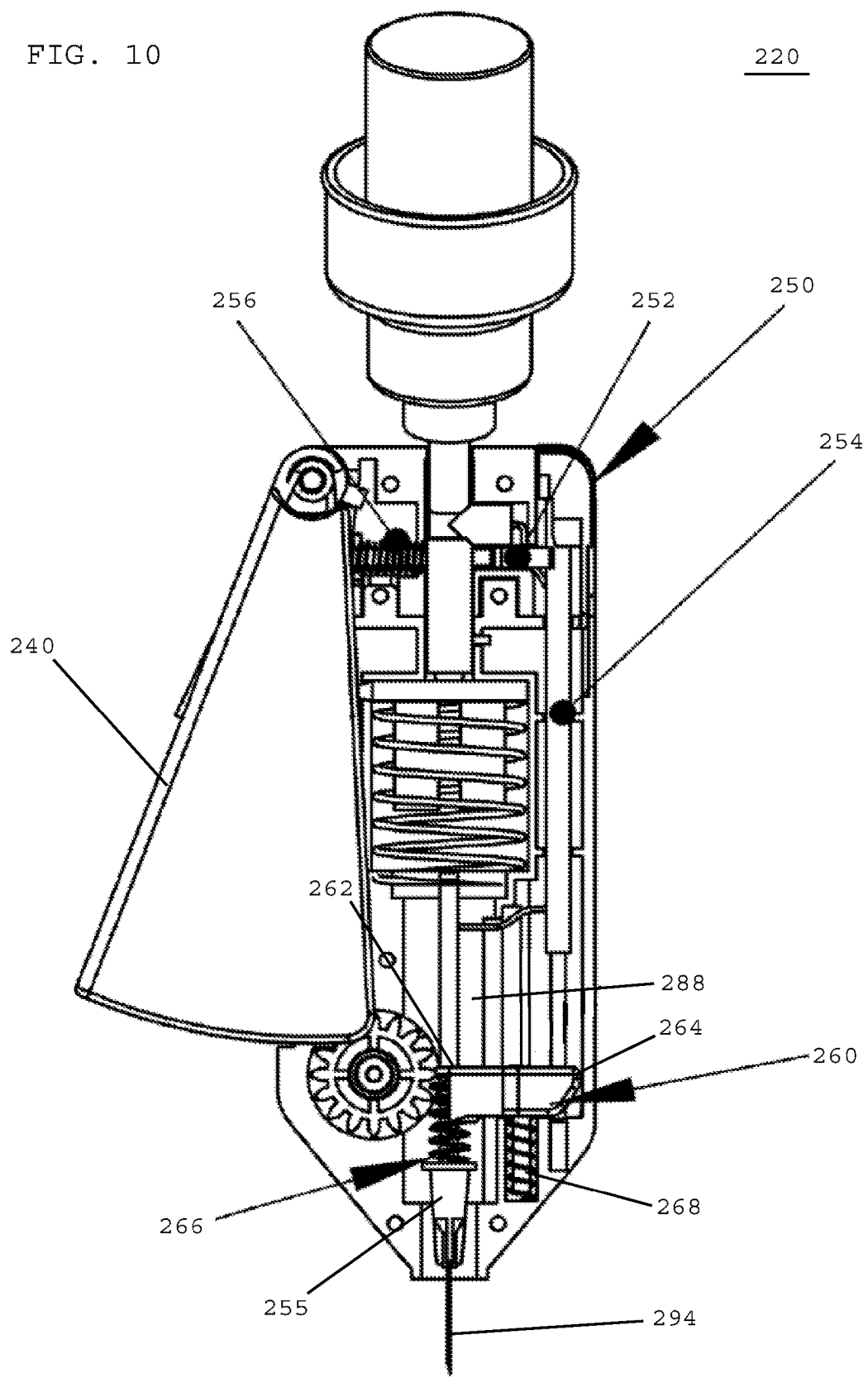
FIG. 10 shows a cross-sectional view of an applicator device including an automatic needle ejection system, in accordance with one embodiment of the present invention.

Referring to FIG. 10, in one embodiment, the drive system 36 desirably includes an internal gear 56 that is coupled with, and rotates simultaneously with, the first and second external gears 54A, 54B. In one embodiment, the first and second external gears 54A, 54B and the internal gear 56 are desirably mounted on an elongated shaft 55 and rotate simultaneously with one another in response to rotation of the elongated shaft. As the handle 40 is pressed in the direction indicated $D_1$, the first and second sets of gear teeth 48A, 48B at the lower end of the handle 40 engage the teeth 52 on the respective first and second external gears 54A, 54B for rotating the external gears in a counterclockwise direction $R_1$. In turn, the rotating first and second external gears 54A, 54B rotate the elongated shaft 55, which rotates the internal gear 56 in a counterclockwise direction. In one embodiment, the lower end of the housing 22 preferably includes a bottom surface 58 having an injection needle opening 60 extending therethrough so that an injection needle (not shown) may be advanced through the injection needle opening.

Figure 2:
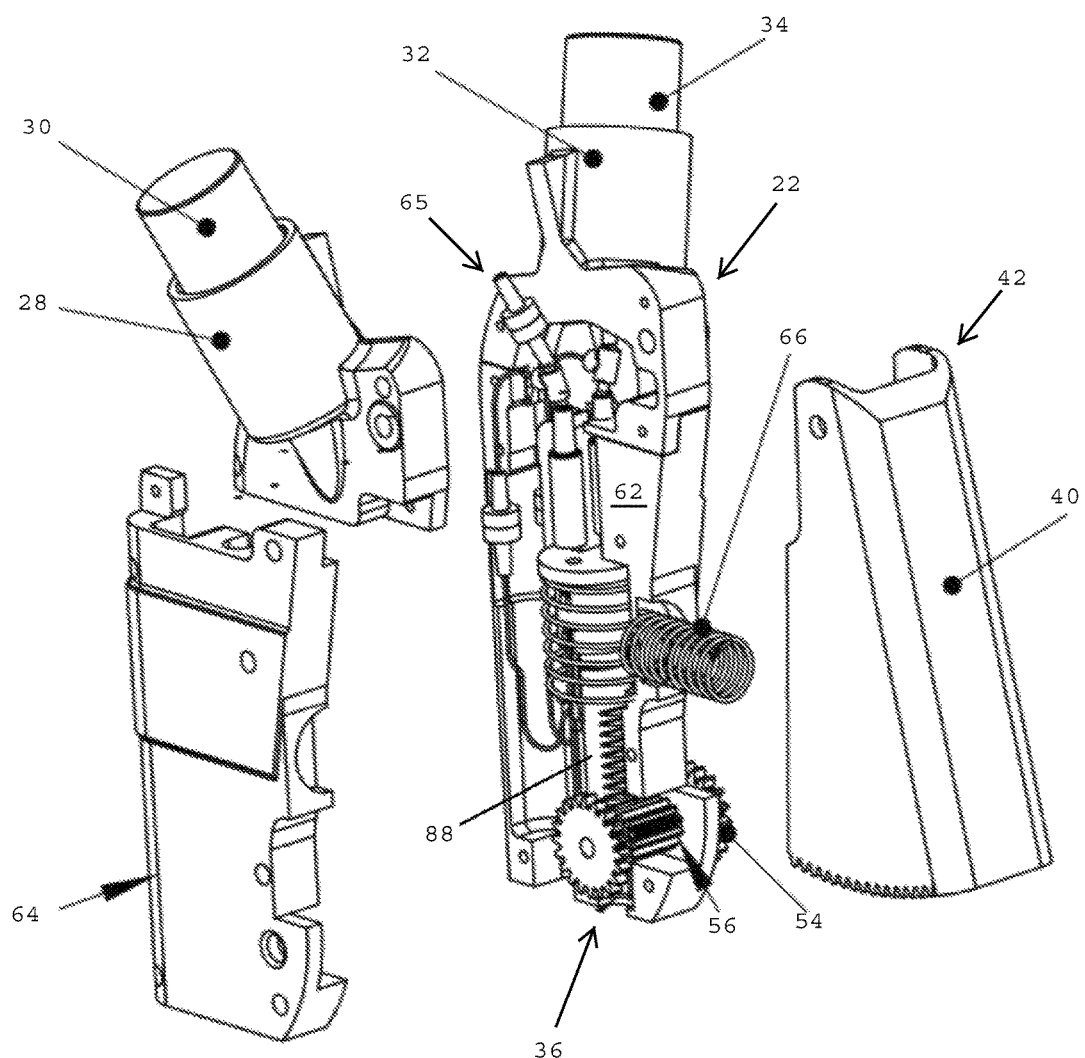
FIG. 2 shows an exploded view of the applicator device shown in FIGS. 1A-1C.

Referring to FIG. 2, in one embodiment, the housing 22 of the applicator device 20 preferably has a main body 62 and a cover 64 that is adapted to be assembled with the main body 62. The main body and the cover preferably have internal surfaces that are adapted to receive and/or seat various parts of the drive system 36 and an injection system 65 for the applicator device.

In one embodiment, the drive system 36 and the injection system 65 are preferably disposed between the cover 64 and the main body 62 of the housing 22. In one embodiment, after the cover 64 and the first vial holder 28 are assembled with the main body 62, an upper end 42 of the handle 40 may be pivotally connected to one or more external surfaces of the housing 22. In one embodiment, the handle 40 may be pressed toward the housing 22 for commencing an injection cycle.

In one embodiment, the applicator device 20 preferably includes a handle spring 66 that extends between an inner surface of the handle 40 and an outer surface of the housing 22. After the handle 40 is pressed for advancing an injection needle from a lower end 26 of the housing 22 to perform an injection, the handle 40 may be released whereupon it is returned to the original position shown in FIGS. 1A-1C under the force of the handle spring 66. In one embodiment, when the handle 40 is pressed toward the housing 22, energy is stored in the handle spring 66. When the handle 40 is released, the energy stored in the handle spring 66 is released for returning the handle 40 to the original position (FIGS. 1A-1C), which, in turn, retracts the injection needle.

Referring to FIG. 3, in one embodiment, the applicator device includes an injection system 65 that operates in cooperation with the drive system 36. In one embodiment, the injection system 65 preferably includes the first vial 30 containing a first liquid component, and the second vial 34 containing a second liquid component. The first vial 30 desirably has a lower end that is in fluid communication with a first one-way check valve 70, which enables the first liquid component to flow therethrough in only one direction. As a result, when the first liquid component is drawn from the first vial 30, it may not return to the first vial through the first one-way check valve 70. In turn, the first one-way check valve 70 is in fluid communication with a first T-connector 72. A lower end of the first T-connector 72 is preferably in fluid communication with a first syringe barrel 74 that desirably receives a first reciprocating plunger 76 having a lower end connected with a plunger base 78.

The injection system 65 preferably includes the second vial 34 having a lower end in fluid communication with a second one-way check valve 80, which enables the second liquid component to flow therethrough in only one direction. As a result, when the second liquid component is drawn from the second vial 34, it may not return to the second vial through the second one-way check valve 80. In turn, the second one-way check valve 80 has a lower end in communication with a second T-connector 82, which is preferably in fluid communication with a second syringe barrel 84 that receives a second reciprocating plunger 86. In one embodiment, each of the lower ends of the first and second reciprocating plungers 76, 86 are desirably connected with or project from the plunger base 78 for moving together with one another and with the plunger base. In one embodiment, the first and second one-way check valves 70, 80 may include a needle assembly preferably adapted to puncture vial septums on the respective first and second vials 30, 34.

In one embodiment, one or more of the vial septums may be punctured by a needle protruding from the vial holder.

In one embodiment, the injection system preferably includes a needle housing 88 having an upper end 90 adapted for being repeatedly coupled and uncoupled from the plunger base 78 and a lower end 92 that carries an injection needle 94. An outer surface of the needle housing 88 desirably includes a rack 96 having a plurality of teeth that extend along the outer surface thereof. The teeth on the internal gear 56 preferably mesh with the rack 96 for selectively moving the needle housing 88 along an axis, such as a vertically extending axis. The injection system 65 preferably includes a plunger spring 98 that is compressible between the plunger base 78 and one or more internal surfaces of the device housing 22 (FIG. 2) for selectively storing energy in the plunger spring.

In one embodiment, the injection system 65 desirably includes a first tube 100 that provides a first fluid path between the first syringe barrel 74 and the injection needle 94 so as to supply a first liquid component to the injection needle. In one embodiment, the first tube 100 has an upper end in fluid communication with the first T-connector 72 and a lower end that passes through an opening 102 in the needle housing 88 for supplying the first liquid component to the injection needle 94. In one embodiment, the first tube 100 preferably includes a one-way check valve 104 that enables the first liquid component to pass in only one direction, i.e., from the upper end to the lower end of the first tube 100.

In one embodiment, the injection system 65 desirably includes a second tube 106 that provides a second fluid path between the second syringe barrel 84 and the injection needle 94 so as to supply a second liquid component to the injection needle. In one embodiment, the second tube 106 has an upper end in fluid communication with the second T-connector 82 and a lower end that passes through the needle housing opening 102 for supplying the second liquid component to the injection needle 94. The second tube 106 desirably includes a second one-way check valve 108 that enables the second liquid component from the second syringe barrel 84 to pass in only one direction, i.e., from the upper end toward the lower end of the second tube 106.

Referring to FIGS. 1A-1C and 3, in one embodiment, as the handle 40 is pressed toward the housing 22, the first and second sets of gear teeth 48A, 48B at the lower end 44 of the handle 40 rotate the first and second external gears 54A, 54B in a counterclockwise direction indicated R$_1$. As the first and second external gears 54A, 54B rotate in the counterclockwise direction, they, in turn, rotate the elongated shaft 55 which rotates the internal gear 56 in a counterclockwise direction. As the internal gear 56 rotates in a counterclockwise direction, the teeth on the internal gear 56 desirably engage the rack 96 on the outer surface of the needle housing 88 for moving the needle housing and the injection needle 94 in a downward direction along an axis of the housing, such as a vertical axis.

In one embodiment, as the needle housing moves downwardly, the needle housing, at some point, pulls the plunger base 78 in the same downward direction. As the plunger base 78 is pulled downwardly, the first plunger 76 is retracted from the first syringe barrel 74, which draws the first liquid component from the first vial 30, through the first one-way check valve 70, through the first T-connector 72, and into the first syringe barrel 74. Simultaneously, the second plunger 86 is retracted from the second syringe barrel 84, which draws the second liquid component from the second vial 34, through the second one-way check valve 80, through the second T-connector 82, and into the second syringe barrel 84.

In one embodiment, as the needle housing 88 is moved in a downward direction by the rotating internal gear 56, the plunger spring 98 is compressed between the plunger base 78 and one or more internal surfaces of the device housing 22. Energy is preferably stored in the plunger spring 98 as the plunger spring in compressed.

As will be described in more detail below, at a certain stage of an injection cycle, the needle housing 88 decouples from the plunger base 78, which frees the plunger base to move in an upward direction via energy provided by the previously compressed plunger spring 98. As the plunger base 78 moves in an upward direction under the energy provided by the compressed plunger spring, the plunger base 78 advances the first and second plungers 76, 86 into the respective first and second syringe barrels 74, 84. As the first plunger 76 moves into the first syringe barrel 74, the first plunger 76 forces the first liquid component from the first syringe barrel 74, through the first T-connector 72 and into the first tube 100 from which it flows downstream through an opening 102 in the needle housing 88. As the first liquid component is forced into the first tube 100, the first one-way check valve 70 preferably prevents the first liquid component from re-entering the first vial 30. Similarly, as the second plunger 86 moves into the second syringe barrel 84, the second plunger 86 forces the second liquid component from the second syringe barrel 84, through the second T-connector 82 and into the second tube 106 where it flows downstream through an opening 102 in the needle housing 88 for being mixed with the first liquid component and dispensed from the injection needle 94. As the second liquid component is forced into the second tube 106, the second one-way check valve 80 preferably prevents the second liquid component from re-entering the second vial 34.

Figure 4A:
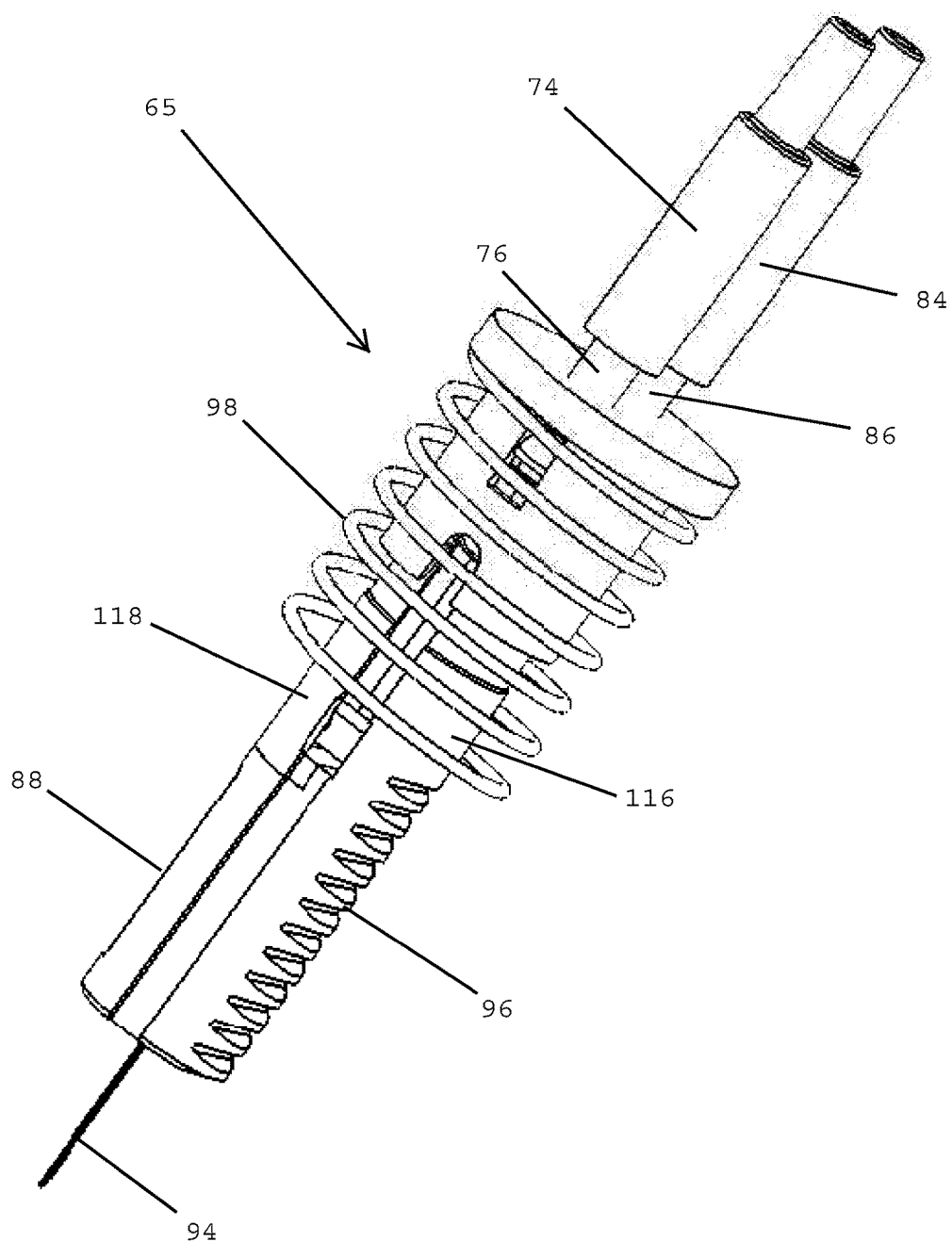
Figure 4B:
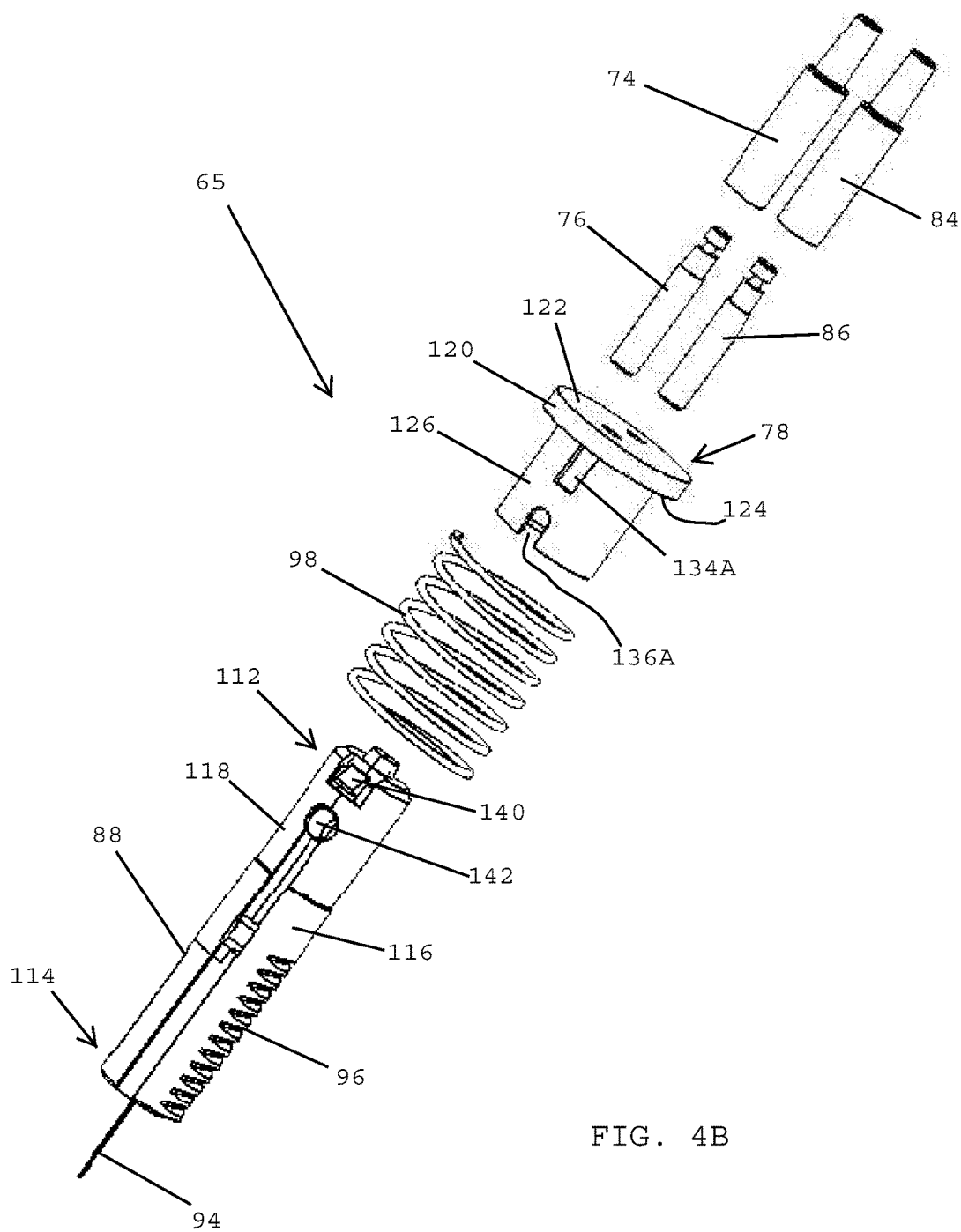

Referring to FIGS. 4A and 4B, in one embodiment, the injection system 65 preferably includes the needle housing 88 having an upper end 112 and a lower end 114. The needle housing 88 desirably includes a main body 116 and a cover 118 that are assembled together. The outer surface of the main body 116 of the needle housing preferably includes the rack 96 that is adapted to mesh with the teeth on the internal gear 56 of the drive system 36 shown in FIG. 3. In one embodiment, the injection needle 94 is disposed within the main body 116 and extends from the lower end 114 of the needle housing 88. In one embodiment, the injection needle is preferably connected to the main body 116 by a luer connection.

The injection system 65 preferably includes the plunger spring 98 that overlies the upper end 112 of the needle housing 88. In one embodiment, the plunger base 78 is preferably adapted to engage an upper end of the plunger spring 98. In one embodiment, when the needle housing 88 is coupled with the plunger base 78 for pulling the plunger base toward the lower end of the applicator device, the plunger spring 98 is preferably compressed between the plunger base 78 and one or more internal surfaces of the housing 22 for storing energy in the plunger spring. In one embodiment, when the plunger base 78 is decoupled from the needle housing 88, energy stored in the plunger spring 98 is released for driving the plunger base 78 upward and away from the lower end of the device.

In one embodiment, the injection system 65 preferably includes the first and second plungers 76, 86 projecting from a top surface of the plunger base 78. The first and second plungers 76, 86 preferably move simultaneously with one another and with the plunger base. The injection system also preferably includes the first and second syringe barrels 74, 84 that are adapted to receive the respective first and second plungers 76, 86. As the plunger base 78 reciprocates up and down, the first and second plungers 76, 86 desirably reciprocate up and down within the syringe barrels 74, 84 for alternatively drawing the liquid components into and dispensing the liquid components from the syringe barrels.

Figure 4C:
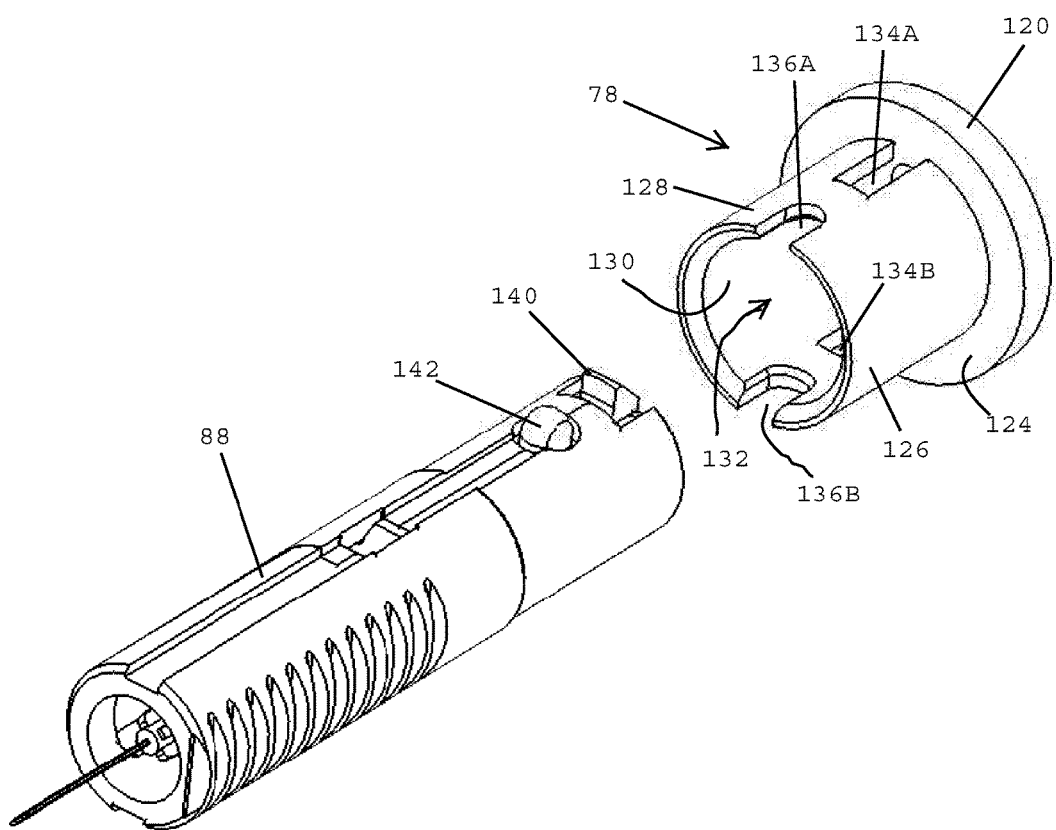

Referring to FIGS. 4B and 4C, in one embodiment, the plunger base 78 preferably includes a disc 120 having a top surface 122 and a bottom surface 124, and a cylinder 126 projecting from the bottom surface 124 of the disc 120. The cylinder 126 preferably has an outer surface 128 and an inner surface 130 defining an elongated bore 132 extending between a lower end of the cylinder 126 and the bottom surface 124 of the disc 120. The elongated bore 132 is adapted to receive an upper end 112 of the needle housing 88 as the needle housing and plunger base are coupled and decoupled from one another. In one embodiment, the cylinder 126 preferably includes two upper slots 134A, 134B adjacent the bottom surface 124 of the disc 120, and two lower slots 136A, 136B that are open at the lower end of the cylinder 126. The two upper slots 134A, 134B are preferably aligned with one another on opposite sides of the cylinder 126. Similarly, the two lower slots 136A, 136B are preferably aligned with one another on opposite sides of the cylinder 126.

In one embodiment, the needle housing 88 preferably includes at least one catch 140 that is adapted for sequentially coupling and decoupling the needle housing 88 and the plunger base 78. In one embodiment, the needle housing preferably includes at least one catch actuator 142 that is coupled with the at least one catch 140 and is adapted for decoupling the needle housing 88 from the plunger base 78. When the needle housing 88 is coupled with the plunger base 78, the at least one catch 140 is preferably engaged with at least one of the two upper slots 134A, 134B, and the at least one catch actuator 142 is preferably aligned with one of the two lower slots 136A, 136B. In one embodiment, when the catch actuator 142 is pressed inwardly, such as by an interior surface of the housing 22, the catch 140 coupled therewith is urged inwardly for decoupling the needle housing 88 and the plunger base 78 from one another.

Figure 4D:
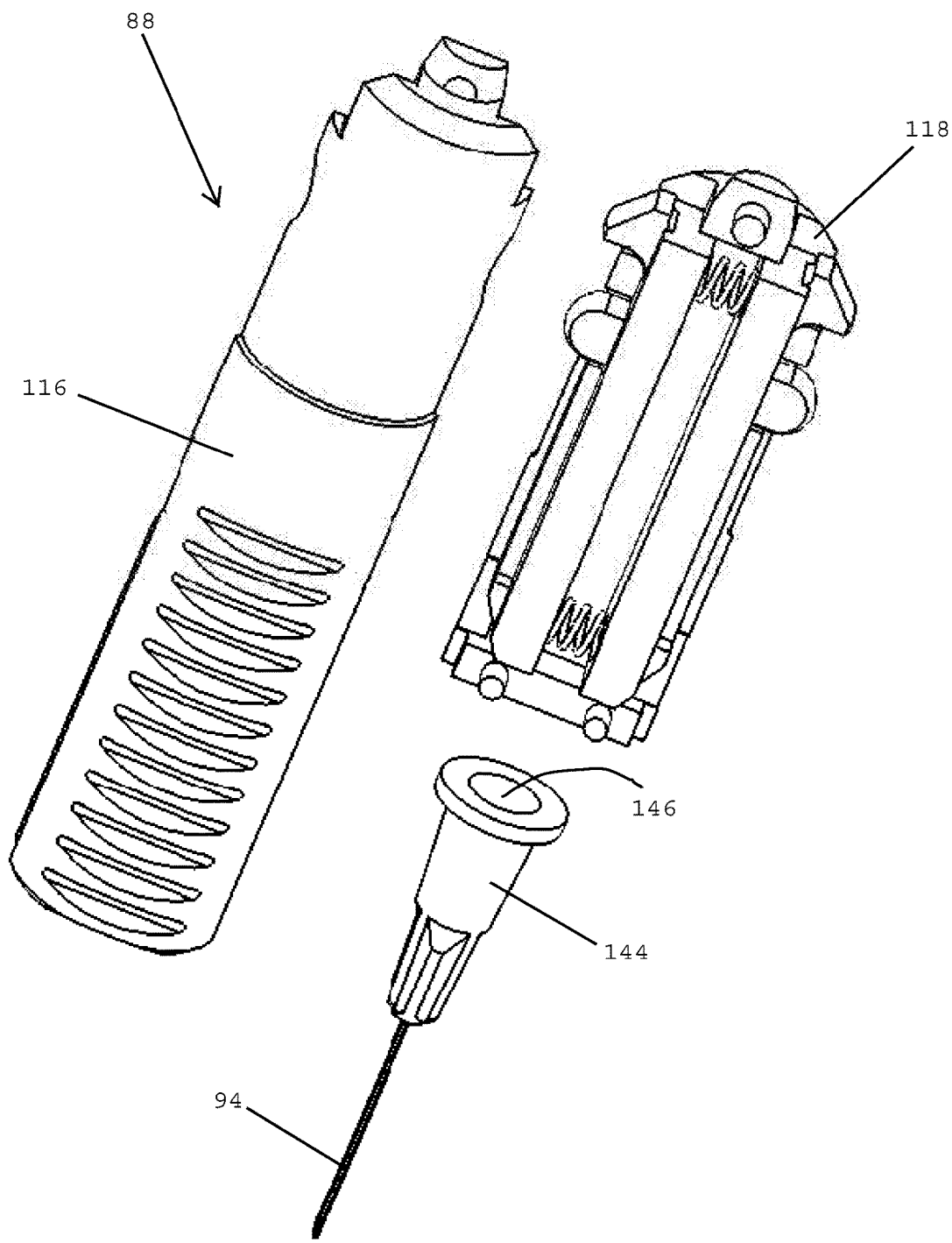

FIG. 4D shows the needle housing 88 after the cover 118 has been disassembled from the main body 116. In one embodiment, the needle housing 88 preferably includes the injection needle 94 having an upper end connected with a needle hub 144. The needle hub 144 preferably has a reservoir opening 146 adapted to receive the distal ends of the first and second tubes 100, 106 (FIG. 3) for receiving the first and second liquid components stored in the first and second vials. In one embodiment, the needle hub 144 is desirably assembled with the main body 116 so that the injection needle 94 projects from the lower end of the needle housing 88. After the injection needle is assembled with the main body 116, the injection needle 94 preferably moves simultaneously with the main body 116 of the needle housing.

Figure 4E:
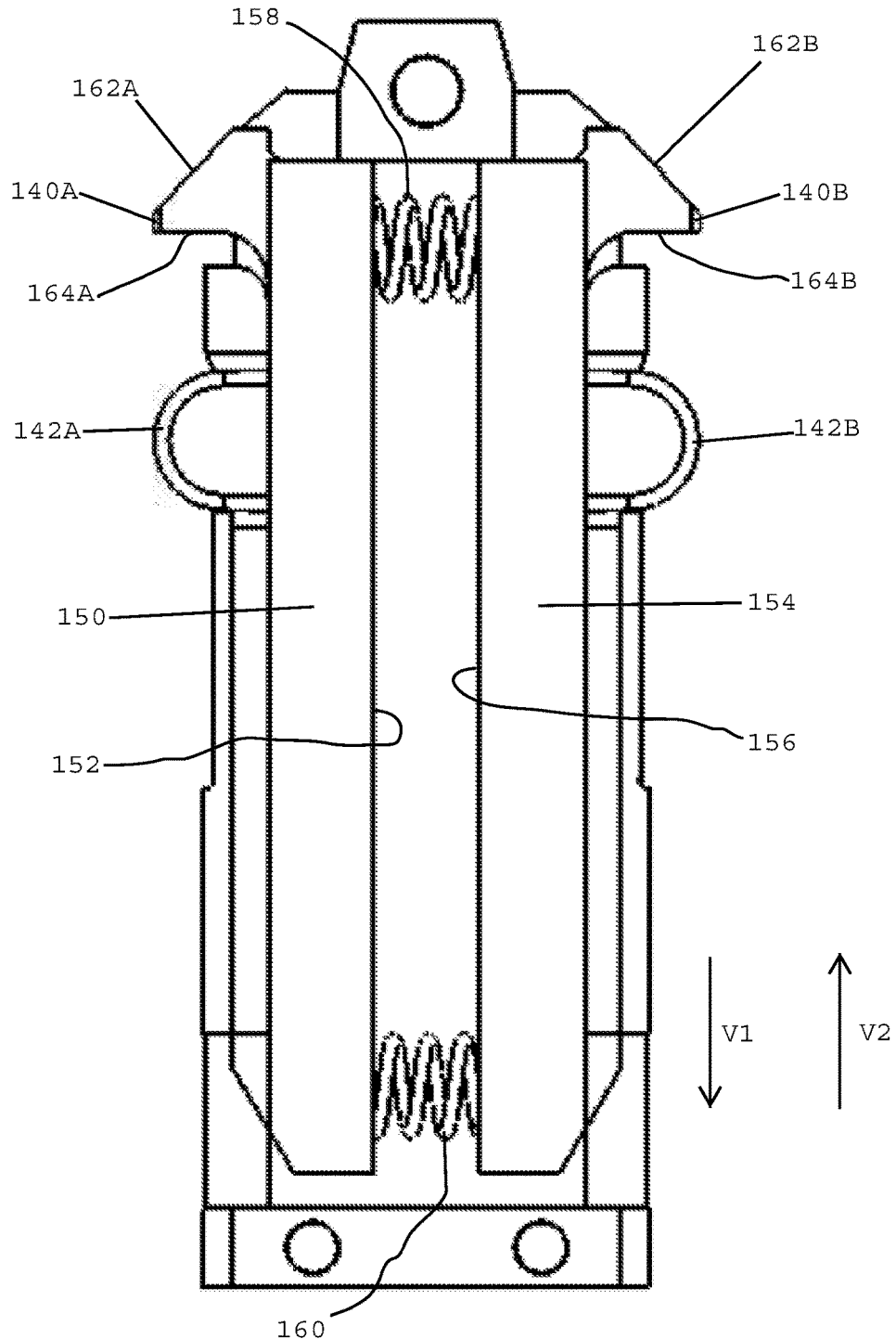

Referring to FIG. 4E, in one embodiment, the cover 118 of the needle housing 88 preferably includes a first elongated element 150 having a first inner surface 152, and an opposing second elongated element 154 having a second inner surface 156 that opposes the first inner surface. In one embodiment, a first spring 158 preferably couples opposing upper ends of the opposing elongated elements 150, 154, and a second spring 160 preferably couples opposing lower ends of the first and second elongated elements 150, 154. In one embodiment, the first and second springs 158, 160 normally urge the first and second elongated elements 150, 154 away from one another.

In one embodiment, the first elongated element 150 includes a first catch 140A connected therewith having a top sloping surface 162A and a bottom, horizontally extending surface 164A. The first elongated element 150 desirably includes a first catch actuator 142A connected thereto. When the first catch actuator 142A is urged inwardly, the first catch 140A connected therewith is also preferably urged inwardly. In one embodiment, the second elongated element 154 preferably includes a second catch 140B having a top sloping surface 162B and a bottom, horizontally extending surface 164B. The second elongated element 154 preferably includes a second catch actuator 142B connected with the second elongated element 154. When the second catch actuator 142B is urged inwardly, the second catch 140B connected therewith is also preferably urged inwardly.

Referring to FIGS. 4E-4F, in one embodiment, during an injection sequence, as the needle housing 88 is initially moved in a downward direction $V_1$ by the drive system 36 (FIG. 2), the catches 140 are seated in the upper slots 134 formed in the cylinder 126 of the plunger base 78. As a result, the needle housing, at one point, pulls the plunger base 78 in the downward direction $V_1$ for compressing the plunger spring 98 and drawing the first and second liquid components into the syringe barrels 74, 84. In one embodiment, there may be lost motion before the plunger base is pulled downwardly for controlling dose volume. Referring to FIG. 4G, in one embodiment, after the needle housing 88 has traveled a predetermined distance in the downward direct $V_1$, the first and second catch actuators 142A, 142B are preferably pressed inwardly by one or more internal surfaces of the housing 22 for urging the first and second elongated elements 150, 154 (FIG. 4E) toward one another. As the first and second elongated elements 150, 154 move toward one another, the first and second springs 158, 160 extending between the elongated elements may be compressed for storing energy therein. As the upper ends of the first and second elongated elements 150, 154 overcome the force of the first spring 158 and move toward one another, the first and second catches 140A, 140B preferably move toward one another so that the first and second catches are decoupled from the two upper slots 134A, 134B formed in the cylinder 126 of the plunger base 78. Once the first and second catches 140A, 140B have been decoupled from the plunger base 78, the needle housing and the plunger base are decoupled so that the plunger spring 98, having energy stored therein drives the plunger base 78 in an upward vertical direction designated $V_2$ for advancing the first and second plungers 76, 86 into the respective first and second syringe barrels 74, 84 so as to dispense the first and second liquid components from the syringe barrels.

Referring to FIG. 4G, as the handle 40 is released for returning to the original start position (FIG. 1A), the drive system 36 moves the needle housing 88 in an upward direction so that the first and second catches 140A, 140B may re-engage with the two upper slots 134A, 134B formed in the cylinder 126 of the plunger base 78 for re-coupling the needle housing with the plunger base 78. In one embodiment, the sloping surfaces 162A, 162B on the respective first and second catches 140A, 140B preferably guide the catches into the upper slots 134A, 134B. Referring to FIGS. 4E and 4F, once the catches 140A, 140B snap back into engagement with the upper slots 134A, 134B, the lower, horizontally extending surfaces 164A, 164B of the catches may maintain the connection between the needle housing 88 and the plunger base 78.

Figure 5A:
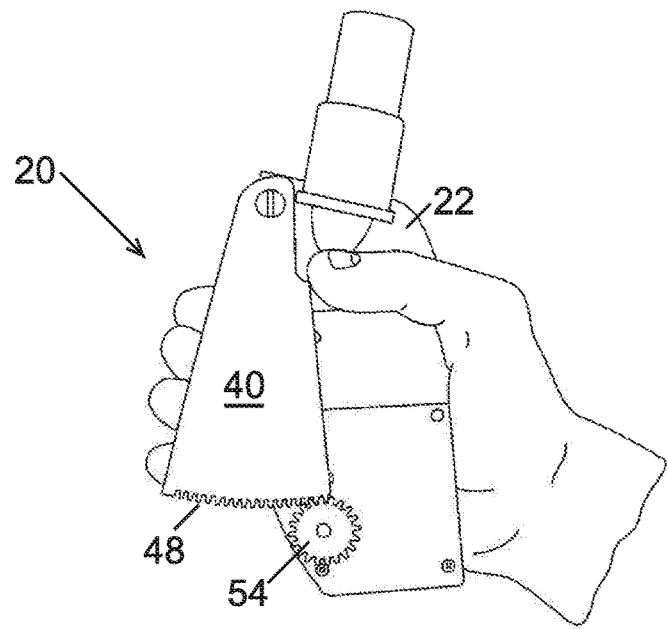
FIGS. 5A-5C show a method of using an applicator device for administering an injection, in accordance with one embodiment of the present invention.
Figure 5B:
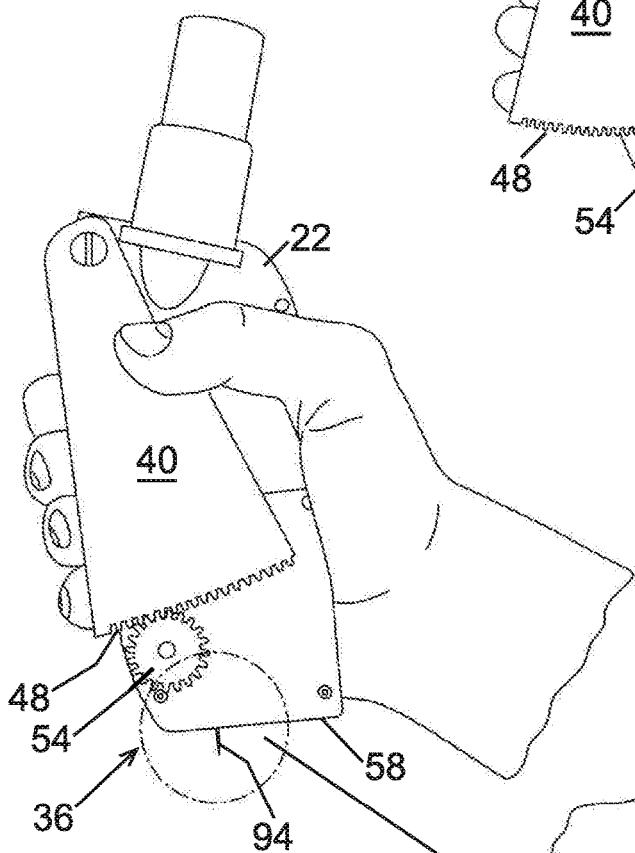
Figure 5C:
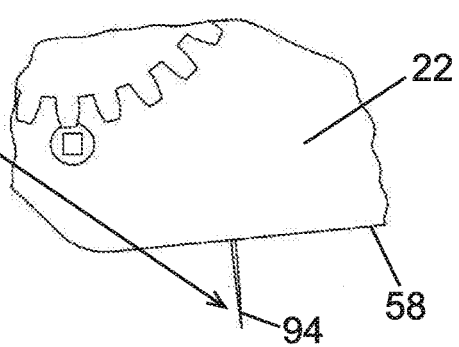

Referring to FIGS. 5A-5C, in one embodiment, the applicator device 20 may be held in an operator's hand with the device housing 22 opposing a palm of the operator's hand and the handle 40 being engaged by the operator's fingers. As shown in FIG. 5A, in one embodiment, the external gear teeth 48 at the lower end of the handle 40 preferably engage the gear teeth on the external gear 54. Referring to FIG. 5B, in one embodiment, the operator may press the handle 40 toward the device housing for commencing an injection cycle for the applicator device 20. Referring to FIGS. 5B and 5C, as the operator squeezes the handle 40, the external gear teeth 48 at the lower end of the handle 40 and the external gear 54 cooperate for advancing an injection needle 94 from the bottom surface 58 of the housing 22.

Referring to FIGS. 6A and 6B, in one embodiment, the first and second catch actuators 142A, 142B normally extend beyond the outer surface of the main body 116 of the needle housing 88. The first and second catch actuators 142A, 142B may be urged towards one another for, in turn, urging the first and second catches 140A, 140B toward one another. Referring to FIG. 6B, in one embodiment, when the first and second catch actuators are forced inwardly, the respective first and second catches 140A, 140B connected therewith are retracted for decoupling the upper end 112 of the needle housing 88 from a plunger base 78.

Referring to FIGS. 7A and 7B, in one embodiment, during a first stage of an injection cycle, as the needle housing 88 is driven in a downward direction $V_1$ by the drive system 36, the horizontal surfaces 164A, 164B of the catches 140A, 140B engage the upper slots 134A, 134B formed in the cylinder 126 of the plunger base 78 for pulling the plunger base with the needle housing 88 in a downward direction. As the plunger base 78 is pulled downward, the plunger spring 98 is compressed, and the first and second plungers are retracted from the first and second syringe barrels for drawing the first and second liquid components into the respective first and second syringe barrels 74, 84. In one embodiment, as the needle housing 88 is driven toward the lower end of the housing 22, the first and second catch actuators 142A, 142B eventually come in contact with one or more internal surfaces 165 of the device housing 22 for moving the catch actuators 142A, 142B inwardly. In turn, the catches 140A, 140B coupled with the catch actuators are retracted until the horizontal surfaces 164A, 164B of the catches 140A, 140B decouple from the upper slots 134A, 134B of the plunger base 78, whereupon the plunger base is free to move in an opposite, upward direction $V_2$ under the force of the compressed plunger spring 98.

After the plunger base 78 has been decoupled from the catches 140A, 140B of the needle housing 88, the plunger base 78 is free, under the energy of the plunger spring, to move in an upward direction $V_2$. As the plunger base 78 moves in the upward direction, the first and second plungers 76, 86 are driven into the respective first and second syringe barrels 74, 84 for forcing the first and second liquid components present in the barrels 74, 84 downstream and into the respective first and second tubes 100, 106 (FIG. 3).

Figure 8:
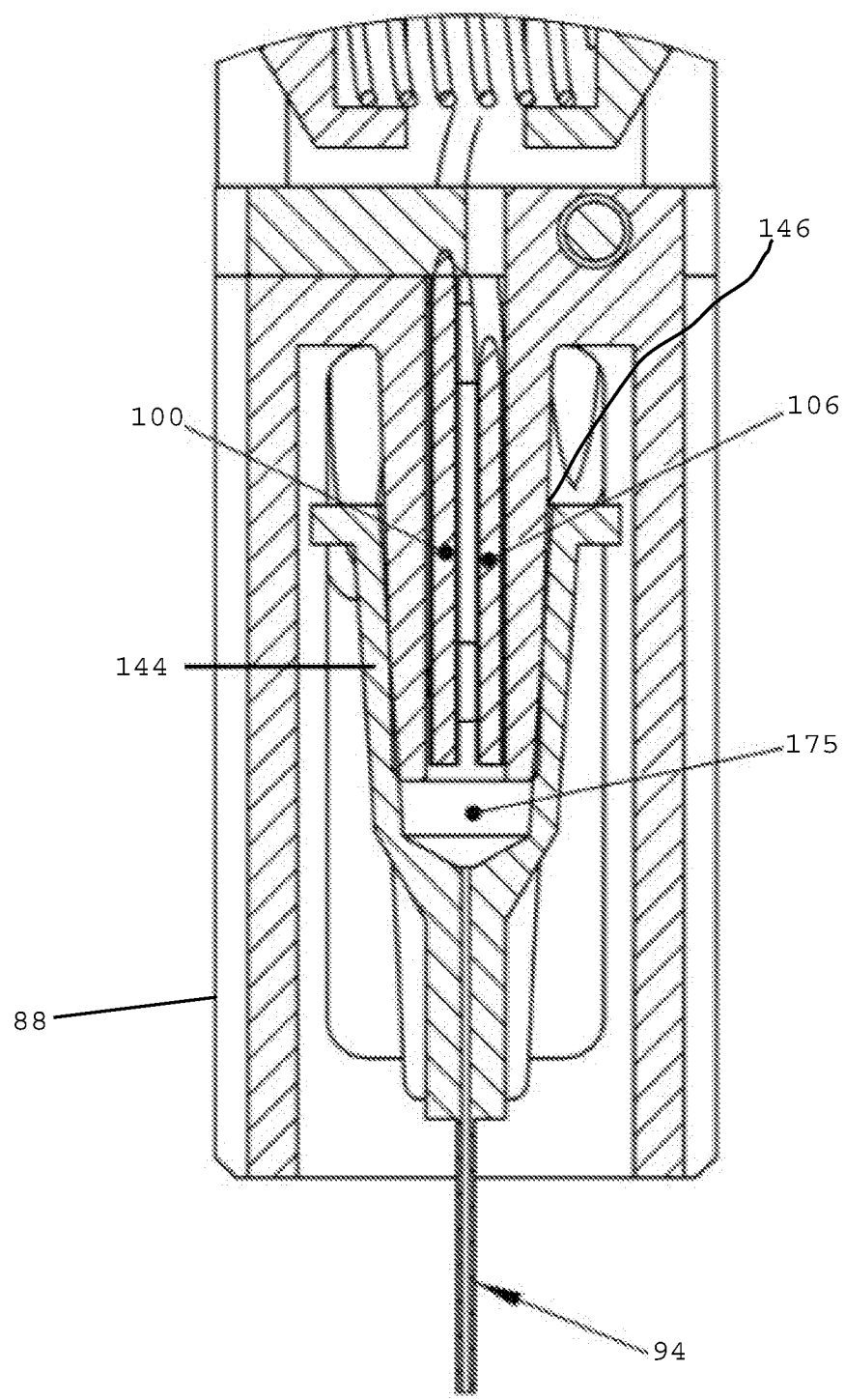
FIG. 8 shows a cross-sectional view of a lower end of a needle housing including a needle hub, a mixing chamber, and an injection needle, in accordance with one embodiment of the present invention.

Referring to FIG. 8, in one embodiment, the injection system 65 preferably includes the needle housing 88 having an injection needle 94 projecting from a lower end thereof. The injection system includes the needle hub 144 coupled with an upper end of the injection needle 94. The needle hub 144 preferably includes a reservoir opening 146 at an upper end thereof that is adapted to receive the distal ends of the first and second tubes 100, 106. The needle hub 144 preferably includes a mixing chamber 175 that is in fluid communication with the distal ends of the first and second tubes 100, 106 so that the first and second liquid components delivered by the first and second tubes 100, 106 may be mixed together in the mixing chamber 175 before being dispensed from the distal end of the injection needle 94.

Although the present invention is not limited by any particular theory of operation, it is believed that providing an applicator device that is able to appropriately mix together at least two different liquid components for injection from a single injection needle 94 and to administer multiple and sequential injections of at least two different liquid components provides many benefits over prior art devices. For example, many prior art injection devices require medical personnel or an individual to use two different injection needles for introducing the two different liquid components into a patient's body. The use of two different injection needles may result in incomplete mixing of the first and second liquid components and misalignment of the first injection needle with the second injection needle at a target location. As a result, the two liquid components may not mix properly, which may have adverse consequences for a patient. The applicator device disclosed herein provides a number of benefits over prior art injection devices including a simple mechanical design that minimizes the number of parts by combining functions and features such as a needle housing 88 that contains the injection needle 94, functions as a drive system 36, and contains the catch 140.

In one embodiment, the injection needle is disposable and may be replaced by a replacement needle. In one embodiment, the injection needle is disposable and includes a needle with a standard luer connection. In one embodiment, the needle may be disposed of automatically such as by providing a pressable button on the device housing and pressing the button for ejecting a first needle and replacing it with a second, replacement needle.

Figure 9A:
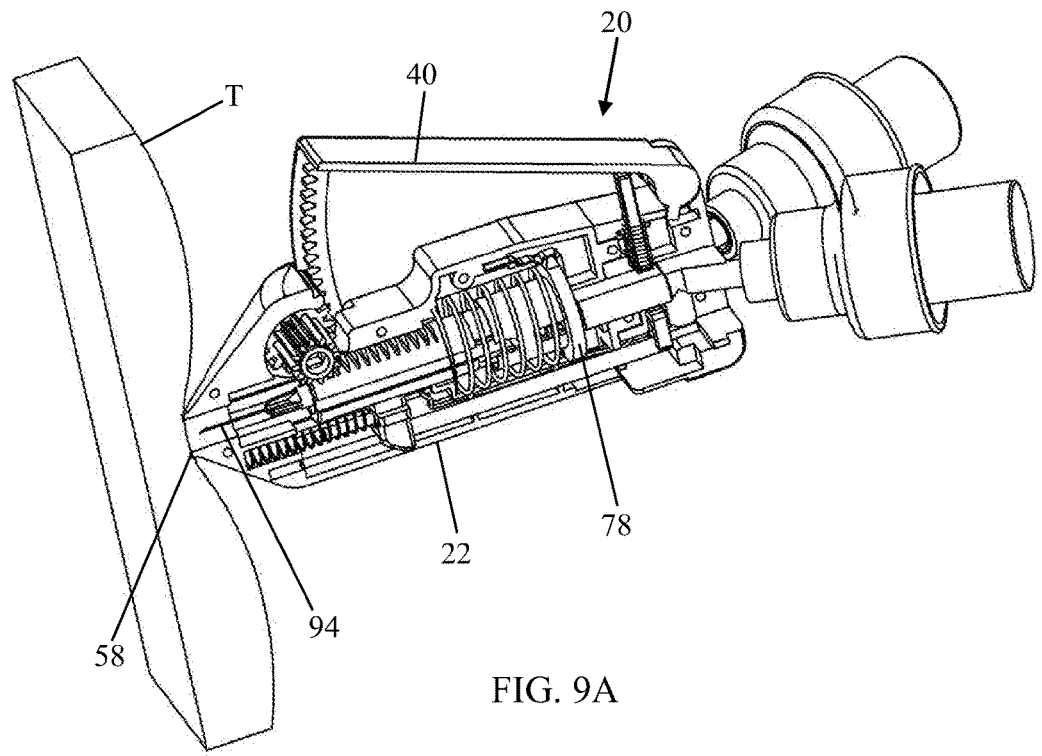
FIGS. 9A-9I show a method using an applicator device for injecting a substance having at least two components into a patient, in accordance with one embodiment of the present invention.

FIGS. 9A-9I show a method of simultaneously injecting at least two liquid components into a patient using a single injection needle, in accordance with one embodiment of the present invention. Referring to FIG. 9A, in one embodiment, with the injection needle 94 fully retracted, the bottom surface 58 of the applicator device 20 is abutted against tissue T of a patient. Prior to commencement of a first stage of an injection cycle shown in FIG. 9A, the handle 40 is fully extended away from the device housing 22, the injection needle 94 is retracted inside the device housing 22, and the first and second plungers 76, 86 projecting from the plunger base 78 are fully advanced into the first and second syringe barrels 74, 84.

Figure 9B:
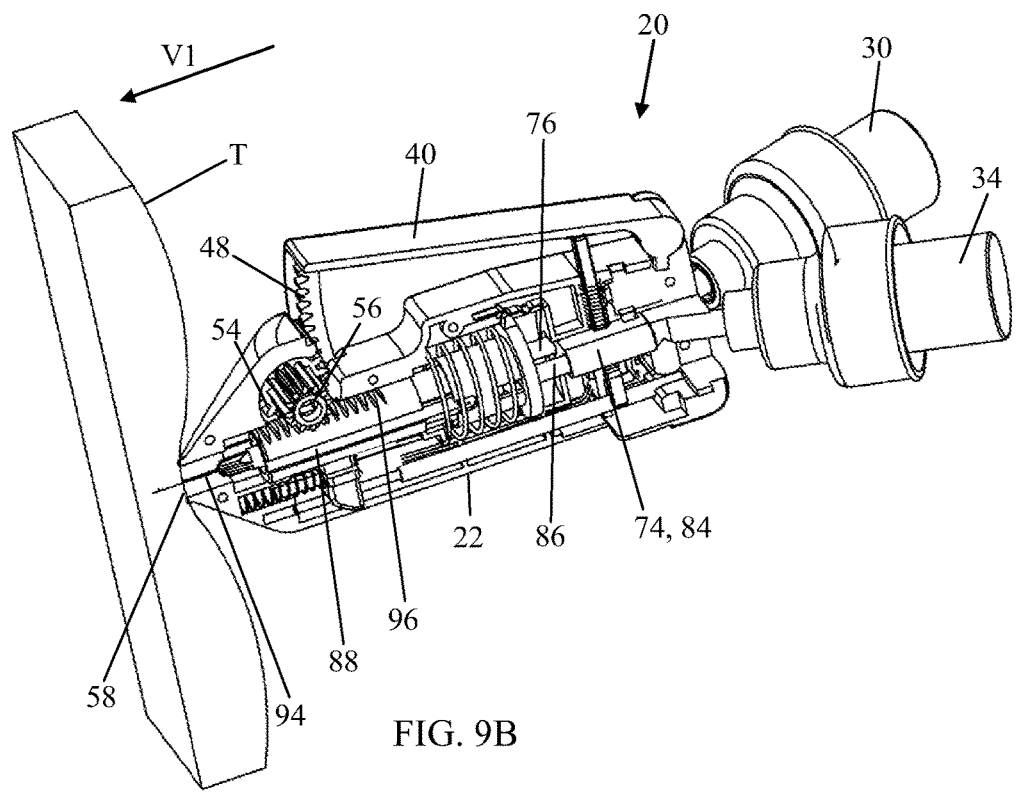

Referring to FIG. 9B, during a first stage of an injection cycle, with the bottom surface 58 of the applicator device 20 abutted against the tissue T, an operator preferably squeezes the handle 40 toward the housing 22 to begin an injection sequence. As the handle 40 is pressed toward the housing 22, the teeth 48 at the lower end of the handle 40 preferably rotate the first and second external gears 54, which, in turn, rotate the internal gear 56. As the internal gear 56 rotates, the teeth of the internal gear 56 engage the rack 96 of the needle housing 88 for moving the needle housing in a direction $V_1$ toward the tissue T. As the needle housing 88 moves toward the tissue T, the injection needle 94 at the lower end of the needle housing preferably advances into the tissue T.

At the same time, as the needle housing 88 moves toward the bottom surface of the applicator device, the needle housing 88, which, at this stage of the injection cycle, is coupled with the plunger base 78, pulls the plunger base 78 toward the bottom surface 58 of the applicator device 20. As the plunger base 78 moves toward the bottom surface 58, the plunger spring 98 is compressed by the plunger base for storing energy in the plunger spring. Moreover, as the plunger base moves toward the lower end, the first and second plungers 76, 86 are withdrawn from the respective first and second syringe barrels 74, 84 for drawing the first and second liquid components from the respective first and second vials 30, 34 for filling the syringe barrels. The plunger spring 98 remains between the bottom surface of the plunger base 78 and one or more inner surfaces of the device housing in a compressed form. As such, the length of the plunger spring 98 is shortened when being compressed, and then returns to its original length as it uncompresses.

Figure 9C:
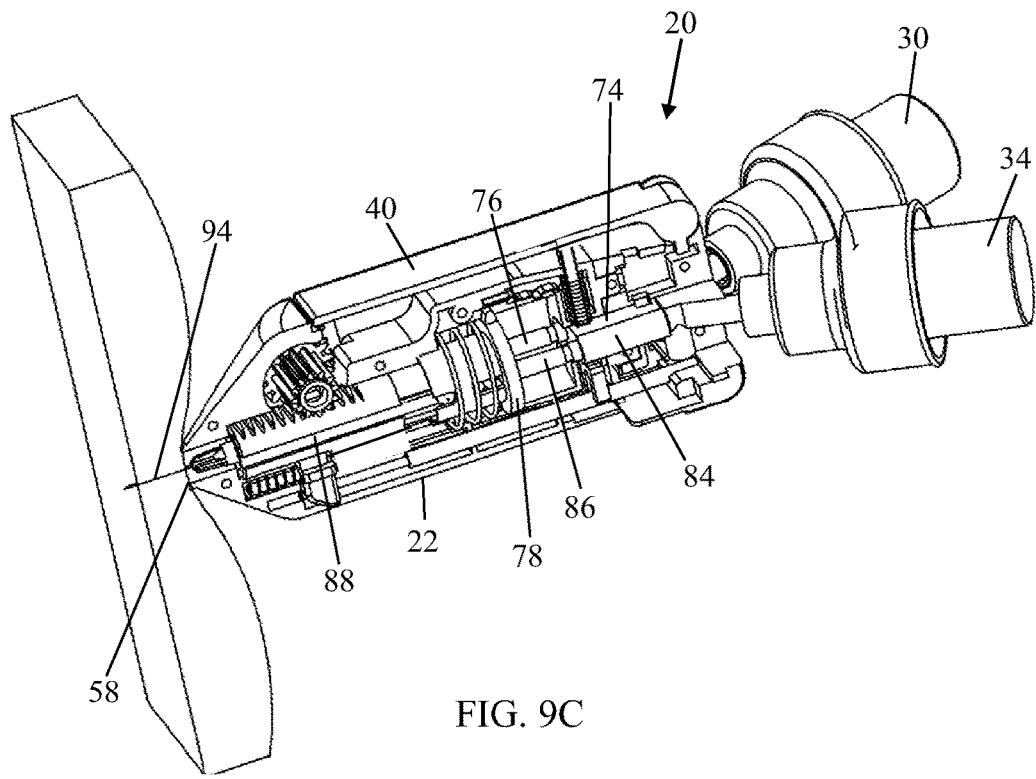

Referring to FIG. 9C, in one embodiment, during a later stage of an injection cycle, the handle 40 is fully squeezed against the housing 22 for further advancing the needle housing 88 toward the bottom surface 58 of the applicator device 20. In one embodiment, when the handle 40 is fully pressed against the housing 22, the injection needle 94 is preferably fully advanced from the bottom surface 58 of the device for insertion into the tissue T. In one embodiment, as the handle 40 is partially compressed, the first and second catches 140A, 140B remain coupled with the plunger base 78 so that the needle housing may continue to pull the plunger base toward the bottom surface 58 of the device housing 22. The plunger spring 98 continues to be compressed between the disc of the plunger base 78 and the inner surfaces of the device housing 22 for storing energy in the plunger spring.

Figure 9D:
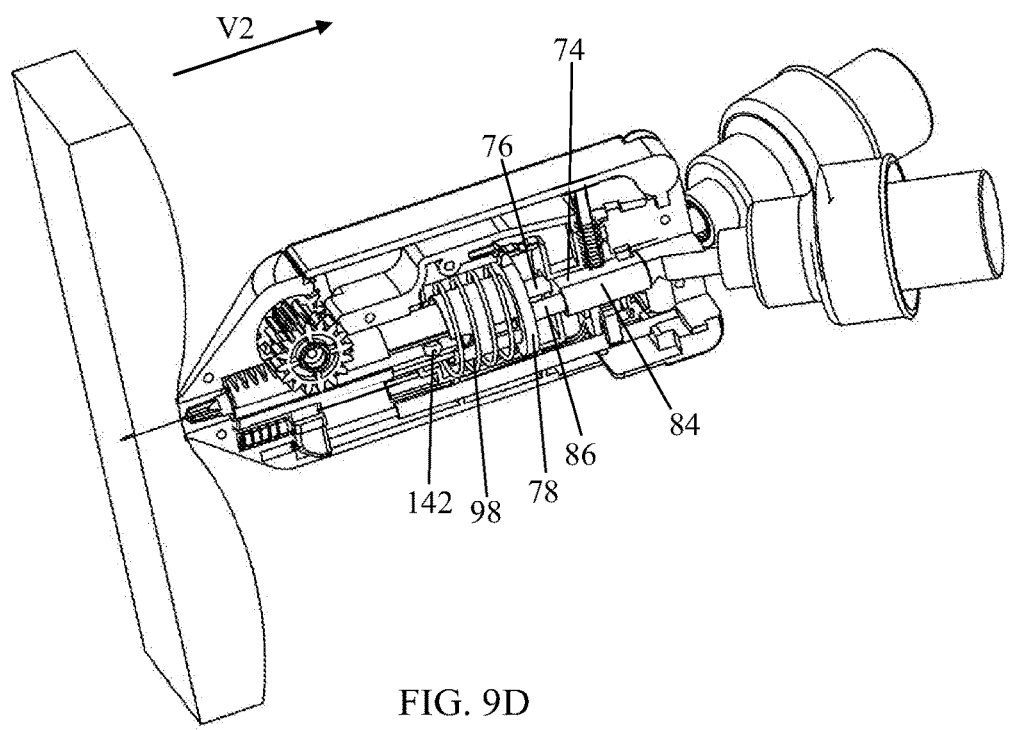

Referring to FIG. 9D, in one embodiment, after the first and second components have been drawn into the first and second syringe barrels 74, 84, the first and second catch actuators 142A, 142B (FIG. 7A) are urged inwardly by the inner surfaces of the housing 22, which, in turn, urges the catches 140A, 140B inwardly for decoupling the needle housing 88 from the plunger base 78. Once the needle housing 88 has been decoupled from the plunger base 78, the force stored in the plunger spring 98 is transmitted to the plunger base 78 for urging the plunger base 78 to move in an upward direction $V_2$. As the plunger base 78 moves in the upward direction $V_2$ under the force of the plunger spring 98, the plunger base 78 urges the first and second plungers 76, 86 into the first and second syringe barrels 74, 84 for dispensing the first and second components into the first and second tubes 100, 106 (FIG. 3) for advancing the first and second components downstream through the first and second tubes.

Figure 9E:
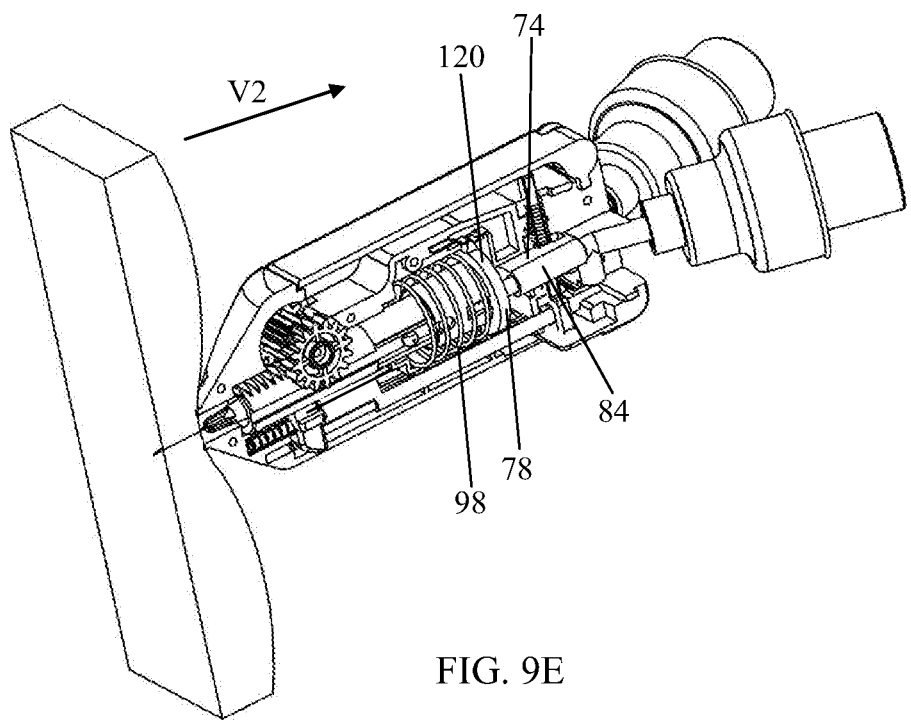
Figure 9F:
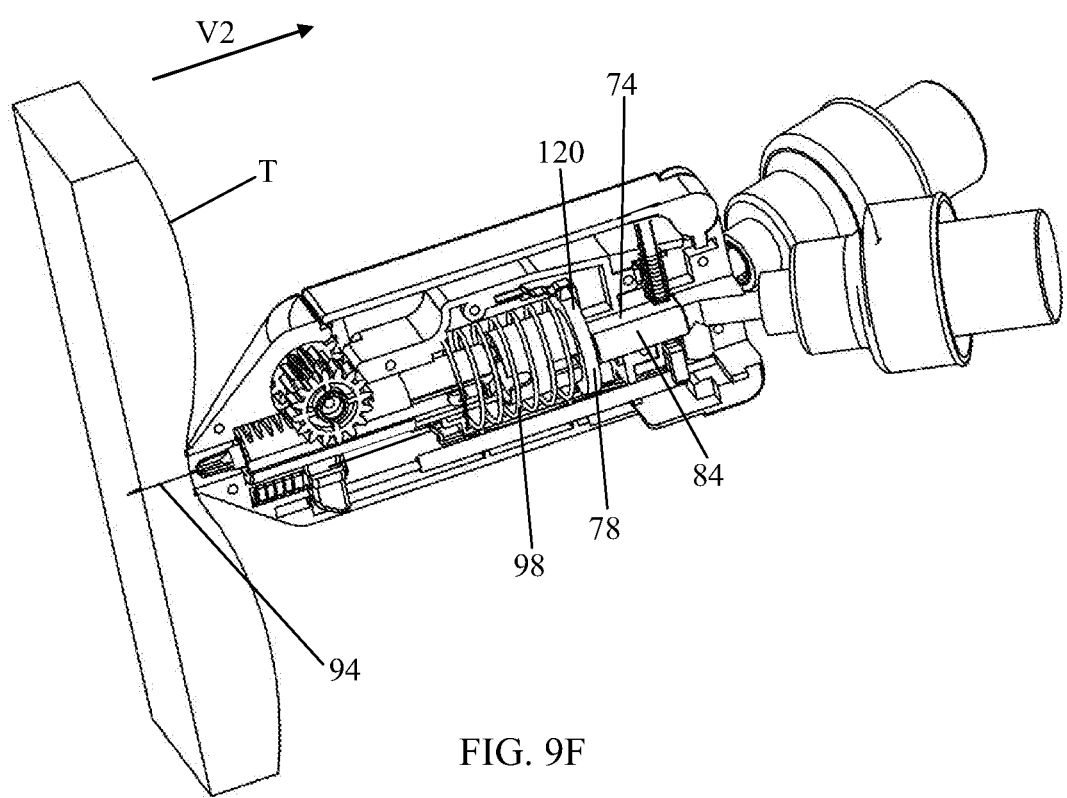

Referring to FIGS. 9E and 9F, in one embodiment, the plunger base 78 is urged in an upward direction $V_2$ by the plunger spring 98 until the top surface 122 of the disc 120 of the plunger base 78 is preferably seated against lower ends of the first and second syringe barrels 74, 84. In one embodiment, when the plunger base 78 is seated against the lower ends of the first and second syringe barrels 74, 84, the first and second components previously drawn into the syringe barrels 74, 84 are evacuated from the syringe barrels and forced into the first and second tubes 100, 106 (FIG. 3). Referring to FIG. 9F, as the plunger base 78 completes its upward journey, the injection needle 94 remains fully inserted in the tissue T so that the mixed solution of the first and second liquid components may be injected into the tissue T. In one embodiment, the injection device is adapted to dispense the solution from the needle only when the needle is fully extended.

Figure 9G:
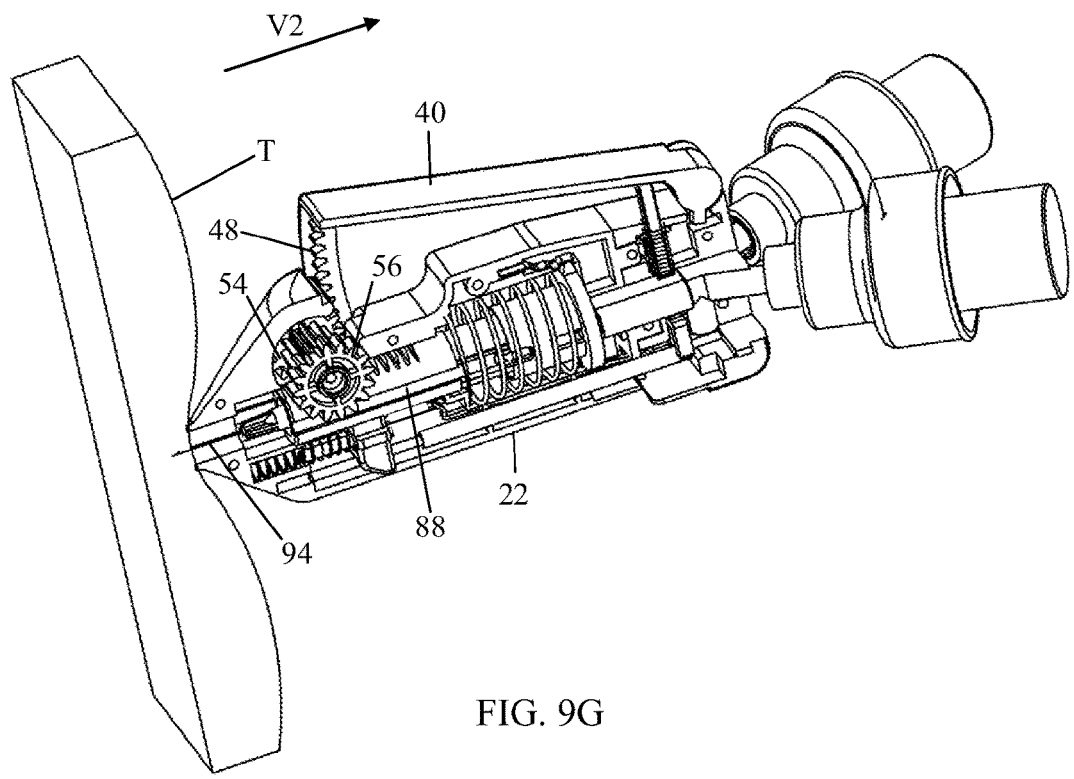
Figure 9H:
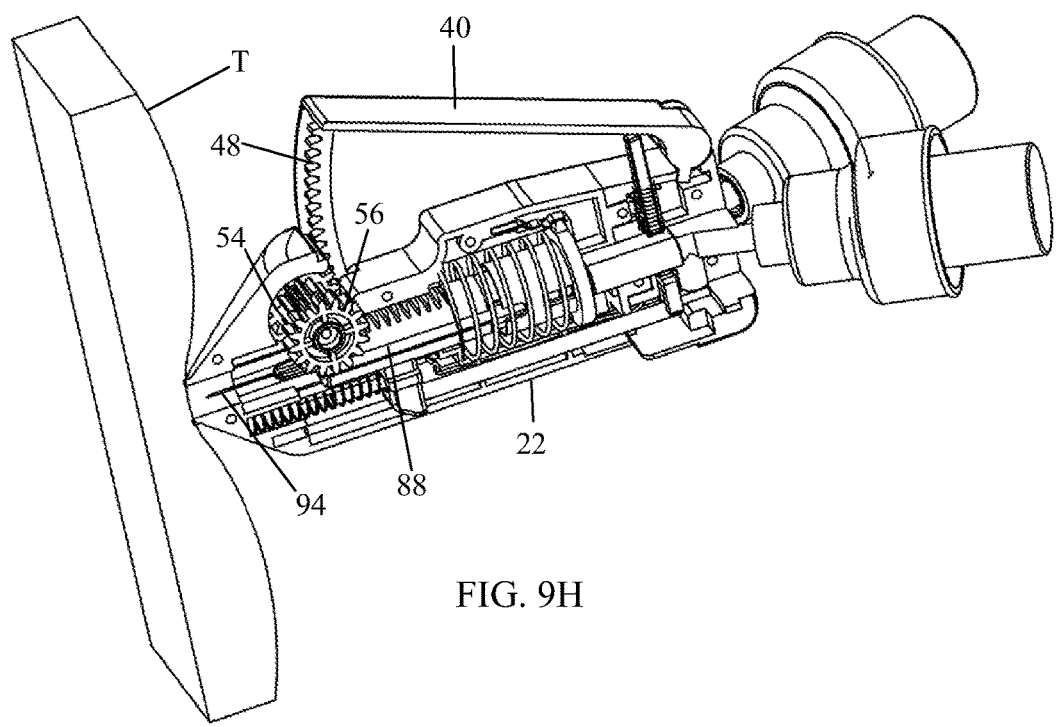

Referring to FIG. 9G, in one embodiment, the needle is extracted from the tissue only when the handle is released by the administrator. In one embodiment, after the mixed first and second liquid components have been injected into the tissue T, the handle 40 may be released for enabling the handle to return to the original start position shown in FIG. 9A. In one embodiment, the handle spring 66 (FIG. 2), previously compressed when the handle 40 was squeezed, now urges the handle 40 to return to the original position shown in FIG. 9A. As the handle 40 returns to the initial or first position, the gear teeth 48 at the lower end 44 of the handle 40 preferably rotate the external gears 54 in an opposite direction, which, in turn, rotate the internal gear 56, which, in turn, drives the needle housing 88 in the upward direction $V_2$. As the needle housing 88 is driven in the upward direction by the drive system 36, the injection needle 94 is withdrawn from the tissue T. FIG. 9H shows the handle 40 during a further stage of the injection cycle with the injection needle 94 fully withdrawn from the tissue T.

Figure 9I:
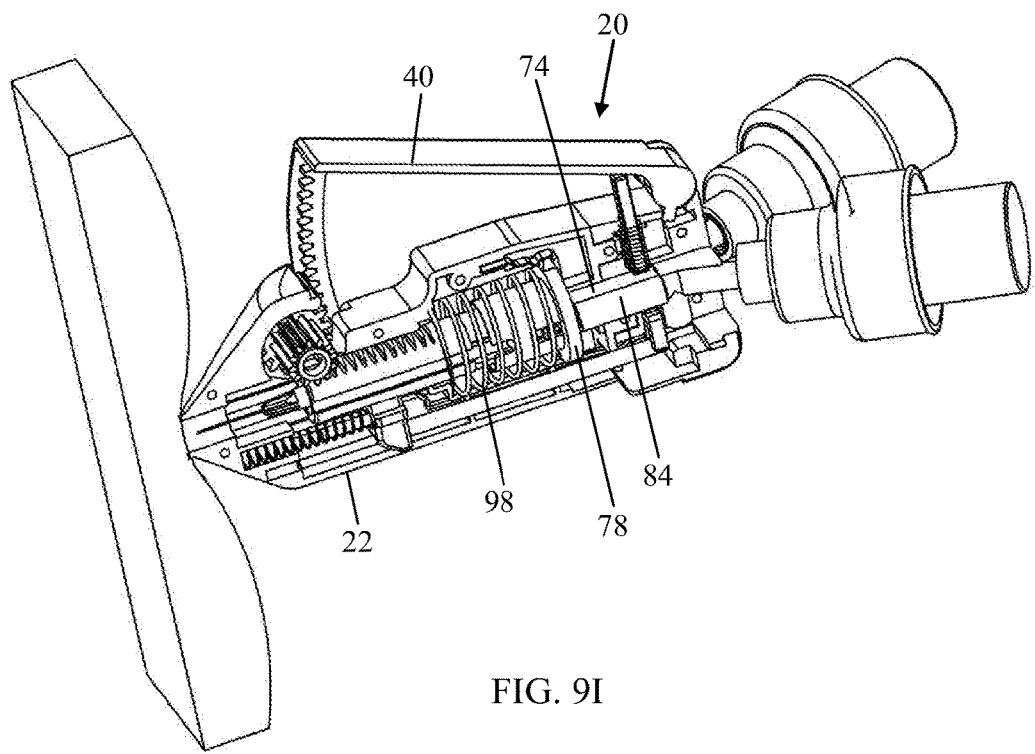

FIG. 9I shows the applicator device 20 after the handle 40 has returned to the original position shown in FIG. 9A. At this stage of the injection cycle, the plunger spring 98 has preferably returned the plunger base 78 to the original start position (FIG. 9A) so that it seats against the lower ends of the of the respective syringe barrels 74, 84. The plunger spring 98 is preferably uncompressed and extends between a lower end of the plunger base 78 and one or more inner surfaces of the device housing 22. The catches 140 at the upper end of the needle housing 88 are desirably coupled with the slots 134 in the cylinder 126 of the plunger base 78 for once again coupling the needle housing 88 with the plunger base 78 so that the needle housing and plunger base are ready for another injection cycle.

In one embodiment, the needle housing preferably travels about 18 mm downwardly so that the injection needle may penetrate into the tissue. In one embodiment, the plunger stroke is approximately 12 mm. In one embodiment, the required dose of each of the liquid components is about 200-500 micro-liters. In one embodiment, the lost motion is about 6 mm. In one embodiment, in order to obtain such parameters, a one milliliter syringe having a diameter of approximately 4.5-15 millimeters may be cut to a length of 10-30 millimeters and installed in the applicator device. In one embodiment, when the needle housing is positioned at the lowest point, the plungers are forced to move up, thereby imposing the flow of the two liquid components from the syringe barrels into the needle. In one embodiment, when the handle is fully squeezed, the plunger spring 98 is uncompressed and the injection needle is fully advanced so that the mixed components may be injected into the tissue.

In one embodiment, the two upper slots 134A, 134B formed in the cylinder 126 below the disc 120 of the plunger base 78 may have lengths that are predetermined to provide for lost motion between the needle housing 88 and the plunger base. In one embodiment, the one or more catches at the upper end of the needle housing initially slide in the upper slots 134A, 134B as the needle housing moves toward the bottom surface of the device housing. Ultimately, the one or more catches engage the lower, closed ends of the two slots 134A, 134B on the plunger base for beginning to pull the plunger base 78 toward the bottom surface of the housing so as to store energy in the plunger spring 98. The term "lost motion" refers to, for example, the distance travelled downwardly by the needle housing before the one or more catches engage the slots of the plunger base. The length of the lost motion can be used to control the volume of the liquid components drawn into the first and second syringe barrels. For example, this length may be changed depending upon the volume of the doses of the first and second components that are desired to be drawn into the first and second syringe barrels. In one embodiment, the "lost motion" length may be increased for drawing less fluid/liquid into the syringe barrels. In one embodiment, the "lost motion" length may be decreased for drawing more fluid/liquid into the syringe barrels.

In one embodiment, the applicator device may be used for administering multiple and sequential injections of an at least two-component substance (e.g. a fibrin sealant such as EVICEL®, QUIXIL®, TISEEL®, BERIPLAST® and the like). In one embodiment, the applicator device preferably enables multiple injections of a fixed-dose of the mixed components on a 2-D surface of a tissue while moving the device. In one embodiment, the injection needle is automatically retracted from the patient's skin after the injection is completed without the need for the administrator to lift the device upward from the injection surface. In one embodiment, the automatic needle extraction is controlled by the administrator. In one embodiment, the device may be used for the administration of fibrin sealant with a fibrinogen component and a thrombin component. In one embodiment, the device may be used for the administration of fibrin sealant with cells for induction of revascularization along a severely ischemic limb, e.g. in diabetic patients. In one embodiment of the invention, the device is used for the administration of a cell suspension. In such an embodiment, the cells are formulated and administered with the fibrinogen component, the thrombin component and/or are administered as a separated component. The administered cells can be isolated from mammalian tissues. In one embodiment of the invention, the device is used for the administration of a viscous component.

Referring to FIG. 10, in one embodiment, an applicator device 220 may include an automatic needle ejection system adapted for disposing an injection needle 294 by engaging an actuator such as an injection needle release button 250. In one embodiment, the needle ejection system preferably has a locked state in which it is impossible to eject an injection needle and an unlocked state in which it is possible to eject an injection needle. In one embodiment, the needle ejection system preferably uses structure similar to that found in pipette tip ejection systems. In one embodiment, the injection needle 294 is coupled with the needle housing 288 via a luer connection.

Figure 11A:
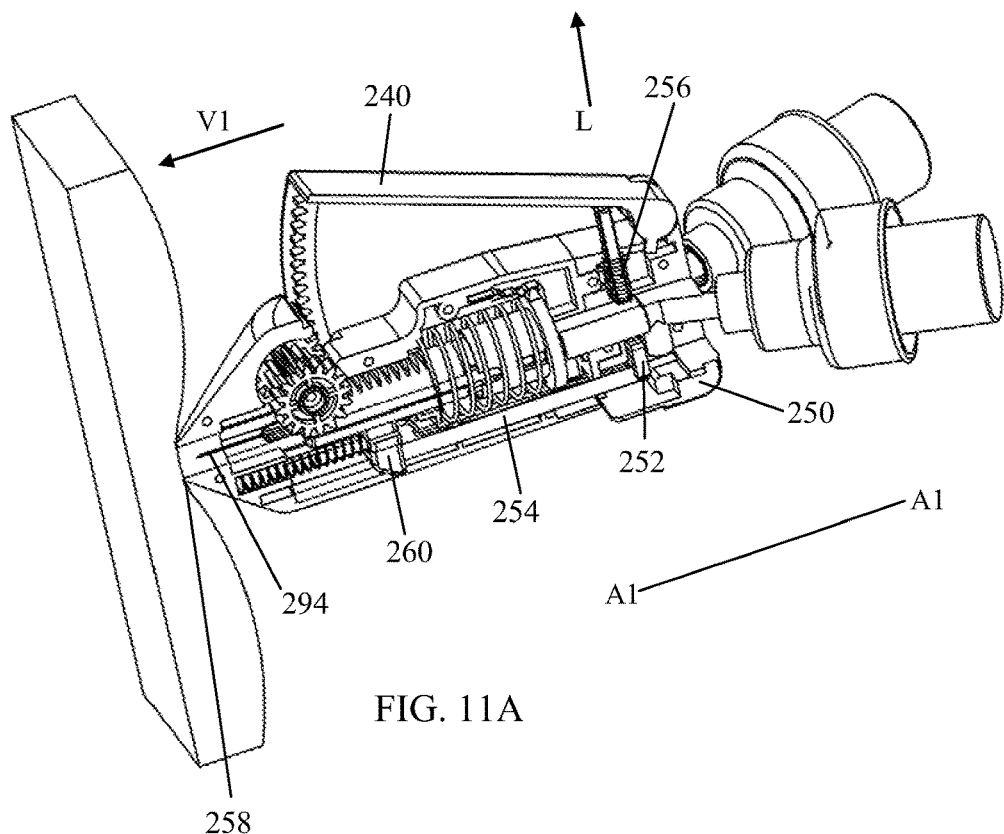
FIGS. 11A-11B show a method of operating the applicator device shown in FIG. 10.
Figure 11B:
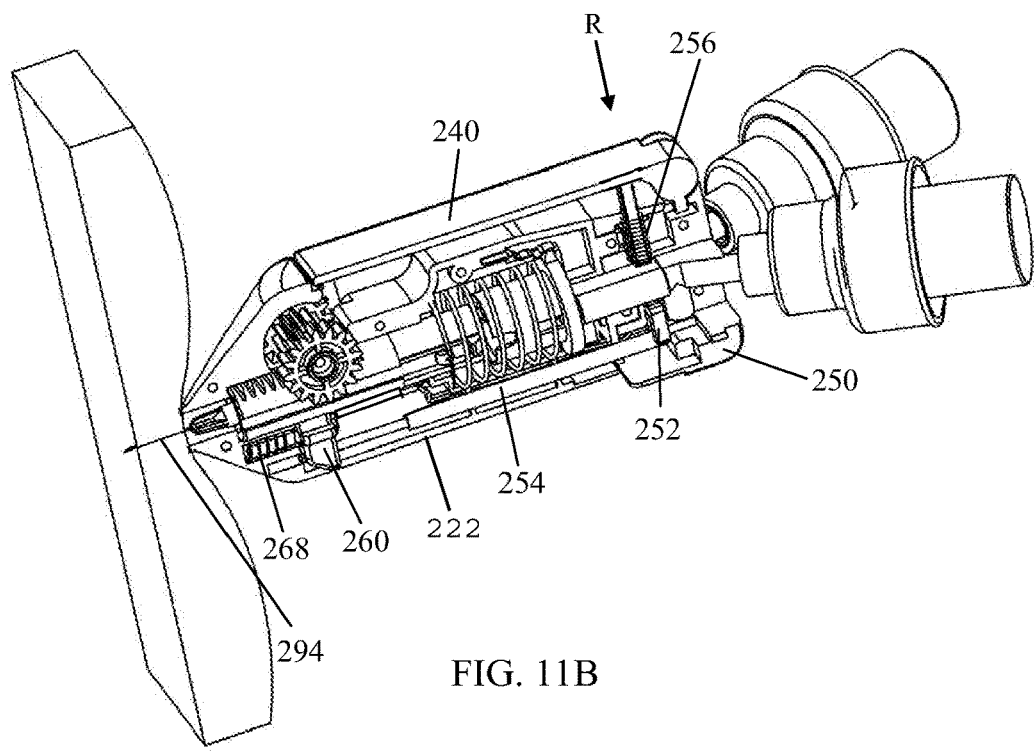

Referring to FIGS. 10, and 11A-11B, in one embodiment, the needle ejection system preferably includes a safety lever fork 252 that extends between a handle 240 and a needle ejection rod 254. In one embodiment, the ejection rod 254 is preferably coupled with the release button 250. In one embodiment, the needle ejection system desirably includes a safety lever spring 256 coupled with the safety lever fork 252. In one embodiment, when the handle 240 is in a first, uncompressed position shown in FIGS. 10 and 11A, the safety lever fork 252 is retracted so that the injection needle release button 250 is unlocked and free to move up and down along an axis $A_1$. In one embodiment, when the handle 240 is pressed toward the device housing 222 as shown in FIG. 11B, an inner surface of the handle 240 desirably engages the safety lever fork 252 for urging the safety lever fork in the direction R so that the safety lever fork 252 engages the injection needle release button 250 for locking the injection needle release button in place, and preventing the release button from being pressed downward along the axis $A_1$. As the safety lever fork 252 is driven in the direction R by the handle 240, the safety lever spring 256 is compressed for storing energy therein. In one embodiment, as long as the safety lever fork 252 remains in contact with the injection needle release button 250 (FIG. 11B), the release button 250 may not be pressed for actuating the needle ejection system for ejecting an injection needle 294. In one embodiment, when the handle 240 is released for returning the handle to the first position shown in FIGS. 10 and 11A, the safety lever spring 256 preferably urges the safety lever fork 252 in the direction L for decoupling the safety lever fork 252 from the injection needle release button 250. As a result, the release button 250 and the rod 254 are free to move along the axis $A_1$.

Referring to FIG. 10, in one embodiment, the needle ejection system preferably includes a fork lever 260 that is coupled with a lower end of the ejection rod 254 for moving simultaneously with the ejection rod along the axis $A_1$. The fork lever 260 preferably has a first end 262 and a second end 264. In one embodiment, the first end 262 is preferably coupled with a needle hub load spring 266 and the second end 264 is preferably coupled with a fork lever spring 268. In one embodiment, when the injection needle release button 250 and the ejection rod 254 are unlocked for being able to move along the axis $A_1$, the ejection rod 254 may be moved in a downward direction $V_1$ for, in turn, moving the fork lever 260 in the direction $V_1$. As the fork lever 260 moves downward, the needle hub load spring 266 and the fork lever spring 268 are compressed and the needle is ejected. In one embodiment, after an injection needle 294 is ejected and the injection needle release button 250 is released, the needle hub load spring 266 and the fork lever spring 268 urge the fork lever 260 upward for, in turn, urging the ejection rod 254 upward.

In one embodiment, the needle ejection system is preferably unlocked when the handle 240 is in the position shown in FIG. 11A and locked when the handle 240 is in the position shown in FIG. 11B. In one embodiment, as the handle 240 is pressed toward the position shown in FIG. 11B, the handle 240 desirably urges the safety lever fork 252 in the direction R. In turn, the safety lever fork 252 is seated against the needle release button 250, which prevents both actuation of the release button 250 and movement of the ejection rod 254 in the direction $V_1$. In one embodiment, when the safety lever fork 252 is in the extended position shown in FIG. 11B, the safety lever fork 252 creates a physical barrier that blocks movement of the release button 250 in the direction $V_1$ so that actuation of the needle ejection system is impossible. In one embodiment, when the safety lever fork 252 is moving in the direction R, the safety lever spring 256 is compressed. After an injection has been made, release of the handle 240 results in movement of the safety lever fork 252 in an opposite direction L under the force of the safety lever spring 256 (FIG. 11A).

When the handle 240 is in the open position shown in FIG. 11A, pressing the release button 250 results in movement of the ejection rod 254 in the direction $V_1$ toward the bottom surface 258 of the device housing 222. In turn, the ejection rod 254 pushes down on the fork lever 260, which, in turn, compresses the fork lever spring 268. At the same time that the fork lever spring 268 is compressed, the needle hub load spring 266 (FIG. 10) that is engaged with the fork lever 260 is also compressed and, in turn, the needle hub 255 (FIG. 10) is ejected from the male luer connection. Release of the release button 250 returns the needle hub load spring 266 and the fork lever spring 268 to their original position.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A device for administering injections comprising:
    a device housing having an upper end and a lower end including a bottom surface with an injection needle opening;
    at least one syringe barrel;
    at least one plunger connected with said at least one syringe barrel;
    a plunger base connected with said at least one plunger, wherein said at least one plunger and said plunger base are adapted for reciprocal movement along an axis;
    a plunger spring in contact with said plunger base;
    a needle housing having an injection needle, said needle housing being adapted for reciprocal movement along said axis;
    an injection actuator for commencing an injection cycle, the injection cycle including
    a first stage in which said needle housing and said plunger base are coupled together and move in a first direction along said axis toward the lower end of said device housing, wherein said plunger base moving in the first direction compresses said plunger spring for storing energy in said plunger spring; and
    a second stage in which said needle housing and said plunger base are decoupled from one another whereupon the energy stored in said plunger spring urges said plunger base to move away from said needle housing in a second direction along said axis toward the upper end of said device housing that is opposite the first direction.

2. The device as claimed in claim 1, wherein said needle housing includes at least one catch projecting from an outer surface thereof for selectively coupling said needle housing and said plunger base together for providing simultaneous movement of said needle housing and said plunger base in a first direction along said axis.

3. The device as claimed in claim 2, further comprising at least one catch actuator coupled with said at least one catch for selectively decoupling said needle housing from said plunger base so that said needle housing and said plunger base are capable of moving independently of one another along said axis.

4. The device as claimed in claim 3, further comprising:
    said injection actuator having gear teeth;
    said needle housing including an outer surface having a rack structure; and
    at least one gear interconnecting said gear teeth of said injection actuator with said rack structure of said needle housing for advancing said needle housing along said axis.

5. The device as claimed in claim 1, further comprising a housing having an upper end, a lower end including a bottom surface with an injection needle opening, wherein said axis extends between said upper and lower ends of said housing.

6. The device as claimed in claim 5, wherein said injection needle is moveable between a retracted position in which said injection needle is disposed within said housing and an extended position in which a distal end of said injection needle extends through said injection needle opening at said bottom surface of said housing.

7. The device as claimed in claim 1, wherein said at least one syringe barrel comprises a first syringe barrel and a second syringe barrel, wherein said at least one plunger comprises a first plunger connected with said first syringe barrel and a second plunger connected with said second syringe barrel, and wherein said plunger base is connected with said first and second plungers and is adapted for moving simultaneously with said first and second plungers.

8. The device as claimed in claim 7, further comprising at least one conduit providing a fluid path between said first and second syringe barrels and said injection needle.

9. The device as claimed in claim 8, wherein said at least one conduit comprises:
    a first conduit in communication with said first syringe barrel for directing a first liquid component toward said injection needle;
    a second conduit in communication with said second syringe barrel for directing a second liquid component toward said injection needle;
    a mixing chamber located between distal ends of said first and second conduits and a proximal end of said injection needle, said mixing chamber being adapted for combining said first and second liquid components into a liquid solution and directing said liquid solution into said proximal end of said needle.

10. The device as claimed in claim 9, further comprising a needle hub connected with a proximal end of said injection needle for connecting said injection needle with said needle housing and directing said first and second liquid components toward said proximal end of said injection needle, wherein said needle hub includes said mixing chamber.

11. The device as claimed in claim 10, further comprising:
    a first reservoir for storing said first liquid component;
    said first conduit having a proximal end in fluid communication with said first reservoir and a distal end in fluid communication with said mixing chamber;
    a second reservoir for storing said second liquid component; and
    said second conduit having a proximal end in fluid communication with said second reservoir and a distal end in fluid communication with said mixing chamber.

12. The device as claimed in claim 11, further comprising:
    said first syringe barrel being in fluid communication with said first conduit, and said first plunger in said first barrel being adapted to alternatively draw said first liquid component into said first barrel and dispense said first liquid component from said first barrel and into said first conduit;
    said second syringe barrel being in fluid communication with said second conduit, and said second plunger in said second barrel being adapted to alternatively draw said second liquid component into said second barrel and dispense said second liquid component from said second barrel and into said second conduit; and
    said plunger base being moveable along said axis of said housing and being connected with said first and second plungers for ensuring simultaneous movement of said first and second plungers between said upper and lower ends of said housing so that said first and second liquid components are simultaneously drawn into and dispensed from said first and second syringe barrels.

13. The device as claimed in claim 12, wherein said first conduit comprises:
    a first one-way check valve for directing flow of said first liquid component in a single downstream direction, said first one-way check valve including an upstream opening coupled with said first reservoir and a downstream opening;

a first T-connector having a first opening in fluid communication with said downstream opening of said first one-way check valve, a second opening in fluid communication with said first syringe barrel, and a third opening; and a first tube having a proximal end in fluid communication with said third opening of said first T-connector and a downstream end in fluid communication with said injection needle, wherein said first liquid component flows between said first and second openings of said first T-connector as said first liquid component is drawn into said first syringe barrel and flows between said second and third openings of said first T-connector and into said proximal end of said first tube as said first liquid component is dispensed from said first syringe barrel; and wherein said second conduit comprises a second one-way check valve for directing flow of said second liquid component in a single downstream direction, said second one-way check valve including an upstream opening coupled with said second reservoir and a downstream opening, a second T-connector having a first opening in fluid communication with said downstream opening of said second one-way check valve, a second opening in fluid communication with said second syringe barrel, and a third opening, and a second tube having a proximal end in fluid communication with said third opening of said second T-connector and a downstream end in fluid communication with said injection needle, wherein said second liquid component flows between said first and second openings of said second T-connector as said second liquid component is drawn into said second syringe barrel and flows between said second and third openings of said second T-connector and into said proximal end of said second tube as said second liquid component is dispensed from said second syringe barrel.

14. A device for administering injections comprising:

a device housing having an upper end and a lower end including a bottom surface with an injection needle opening;

a needle housing including an injection needle, said needle housing being moveable along an axis between a retracted position in which said injection needle is disposed within said device housing and an extended position in which said injection needle extends through said injection needle opening;

said device including a first syringe barrel and a first plunger connected therewith, a second syringe barrel and a second plunger connected therewith, and at least one fluid path between said first and second syringe barrels and said injection needle;

a plunger base connected with said first and second plungers and being adapted for moving simultaneously with said first and second plungers along said axis;

a plunger spring in contact with said plunger base;

an injection actuator for commencing an injection cycle, the injection cycle including a first stage in which said needle housing and said plunger base are coupled together and move in a first direction along said axis toward the lower end of said device housing, wherein said plunger base moving in the first direction compresses said plunger spring for storing energy in said plunger spring; and a second stage in which said needle housing and said plunger base are decoupled from one another whereupon the energy stored in said plunger spring during the first stage urges said plunger base to move away from said needle housing in a second direction along said axis toward the upper end of said device housing that is opposite the first direction.

15. The device as claimed in claim 14, wherein said needle housing includes at least one catch projecting from an outer surface thereof for selectively coupling said needle housing and said plunger base together during the first stage for providing simultaneous movement of said needle housing and said plunger base in the first direction along said axis.

16. The device as claimed in claim 15, further comprising at least one catch actuator coupled with said at least one catch for selectively decoupling said needle housing from said plunger base during the second stage so that said needle housing and said plunger base are capable of moving independently of one another along said axis.

17. The device as claimed in claim 16, further comprising:

said injection actuator having gear teeth;

said needle housing including an outer surface having a rack structure; and at least one gear interconnecting said gear teeth of said injection actuator with said rack structure of said needle housing for advancing said needle housing along said axis.

18. The device as claimed in claim 17, wherein said axis extends between said upper and lower ends of said housing, and wherein in the retracted position said injection needle is disposed within said housing and in the extended position a distal end of said injection needle extends through said injection needle opening at said bottom surface of said housing.

19. A device for administering injections comprising:

a device housing having an upper end and a lower end including a bottom surface with an injection needle opening;

at least one reservoir containing a liquid component;

at least one syringe barrel in fluid communication with said at least one reservoir;

at least one plunger connected with said at least one syringe barrel and being moveable in a first direction along an axis for drawing said liquid component into said at least one syringe barrel;

a plunger base connected with said at least one plunger;

a plunger spring in contact with said plunger base;

a needle housing adapted for reciprocal movement along said axis, said needle housing including a catch projecting from an outer surface thereof for coupling said needle housing and said plunger base together;

a catch actuator coupled with said at least one catch for selectively decoupling said needle housing from said plunger base;

an actuator for commencing an injection cycle, the injection cycle including a first stage in which said needle housing and said plunger base are coupled together by said catch and move is the first direction along said axis toward the lower end of said device housing whereupon said plunger base compresses said plunger spring for storing energy in said plunger spring;

a second stage in which said plunger base is decoupled from said needle housing, whereupon the energy stored in said plunger spring during the first stage urges said plunger base in a second direction along said axis toward the upper end of said device housing that is opposite the first direction for driving said at least one plunger into said at least one syringe barrel.

20. The device as claimed in claim 19, further comprising:
said at least one syringe barrel including a first syringe barrel and a second syringe barrel;
said at least one plunger including a first plunger connected with said first syringe barrel and a second plunger connected with said second syringe barrel, wherein said plunger base is connected with said first and second plungers and is adapted for moving simultaneously with said first and second plungers;
said needle housing including an injection needle;
a first conduit in communication with said first syringe barrel for directing a first liquid component toward said injection needle;
a second conduit in communication with said second syringe barrel for directing a second liquid component toward said injection needle;
a mixing chamber located between distal ends of said first and second conduits and a proximal end of said injection needle, said mixing chamber being adapted for combining said first and second liquid components into a liquid solution and directing said liquid solution into said proximal end of said needle.

* * * * *